US012758724B2

(12) United States Patent
Zhi et al.

(10) Patent No.: US 12,758,724 B2
(45) Date of Patent: Oct. 13, 2026

(54) NOISE REDUCTION STRUCTURE FOR VENTILATION TREATMENT DEVICE AND VENTILATION TREATMENT DEVICE

(71) Applicant: BMC MEDICAL CO., LTD., Beijing (CN)

(72) Inventors: Jianxin Zhi, Beijing (CN); Jie Zhang, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 1141 days.

(21) Appl. No.: 17/790,137

(22) PCT Filed: Nov. 2, 2020

(86) PCT No.: PCT/CN2020/125857
§ 371 (c)(1),
(2) Date: Jun. 30, 2022

(87) PCT Pub. No.: WO2021/135615
PCT Pub. Date: Jul. 8, 2021

(65) Prior Publication Data

US 2023/0233780 A1 Jul. 27, 2023

(30) Foreign Application Priority Data

Dec. 30, 2019 (CN) ........................ 201911398517.X

(51) Int. Cl.
*A61M 16/00* (2006.01)
*F04D 29/66* (2006.01)

(52) U.S. Cl.
CPC .... *A61M 16/0003* (2014.02); *A61M 16/0066* (2013.01); *F04D 29/665* (2013.01)

(58) Field of Classification Search
CPC .......... A61M 16/0003; A61M 2205/42; A61M 16/0066; A61M 2205/75; F04D 29/664;
(Continued)

(56) References Cited

U.S. PATENT DOCUMENTS 6,804,360 B1 * 10/2004 Misawa ............. F02M 35/1255 381/86
7,789,194 B2 * 9/2010 Lathrop .............. A61M 16/024 181/252

(Continued)

FOREIGN PATENT DOCUMENTS

CN 202314809 U 7/2012
CN 103442760 A 12/2013

(Continued)

OTHER PUBLICATIONS

EspaceNet Translation Wang CN206694330 (Year: 2017).*

(Continued)

*Primary Examiner* — Victoria Murphy
*Assistant Examiner* — Sydney Reyes Russell
(74) *Attorney, Agent, or Firm* — Bayramoglu Law Offices LLC

(57) ABSTRACT

A noise reduction structure for a ventilation treatment device and the ventilation treatment device are provided. The noise reduction structure comprises a first micropore plate; the first micropore plate has a first plate surface and a second plate surface which are opposite to each other, the first plate surface is used for forming a first chamber; the second plate surface is used for forming an air passage such that air in the air passage flows along the second plate surface; the first micropore plate has a plurality of first micro-vias through which the first chamber communicates with the air passage. The noise reduction structure is wide in noise reduction frequency band, may effectively reduce aerodynamic noise (Continued)

in the air passage, and improves the satisfaction degree of a patient using the ventilation treatment device.

10 Claims, 27 Drawing Sheets

(58) Field of Classification Search
CPC ...... F04D 29/665; F24F 2013/242–247; F24F 13/24
See application file for complete search history.

(56) References Cited

U.S. PATENT DOCUMENTS

| | | | | |
|---|---|---|---|---|
| 2008/0127976 | A1 | 6/2008 | Acker et al. | |
| 2008/0257346 | A1 | 10/2008 | Lathrop et al. | |
| 2009/0007912 | A1 | 1/2009 | Lindell et al. | |
| 2011/0226245 | A1 | 9/2011 | Gillespie et al. | |
| 2014/0299406 | A1 * | 10/2014 | Librett | A61M 16/0858 181/224 |
| 2016/0310691 | A1 * | 10/2016 | Bath | G16H 20/40 |
| 2017/0203064 | A1 * | 7/2017 | Suzuki | A61M 16/107 |

FOREIGN PATENT DOCUMENTS

| | | | |
|---|---|---|---|
| CN | 203584917 | U | * 5/2014 |
| CN | 203706661 | U | 7/2014 |
| CN | 104132003 | A | 11/2014 |
| CN | 204337452 | U | 5/2015 |
| CN | 204446853 | U | 7/2015 |
| CN | 105194778 | A | 12/2015 |
| CN | 205055109 | U | 3/2016 |
| CN | 106345025 | A | 1/2017 |
| CN | 205956027 | U | 2/2017 |
| CN | 106730203 | A | 5/2017 |
| CN | 206503255 | U | 9/2017 |
| CN | 206566315 | U | 10/2017 |
| CN | 206592305 | U | 10/2017 |
| CN | 206652062 | U | 11/2017 |
| CN | 206694330 | U | * 12/2017 |
| CN | 206730236 | U | 12/2017 |
| CN | 207323803 | U | 5/2018 |
| CN | 108292498 | A | 7/2018 |
| CN | 109038293 | A | 12/2018 |
| CN | 209204371 | U | 8/2019 |
| CN | 110831650 | A | 2/2020 |
| CN | 110975094 | A | 4/2020 |
| JP | H07255850 | A | 10/1995 |
| JP | H08141087 | A | 6/1996 |
| JP | 2001276224 | A | 10/2001 |
| JP | 2008184967 | A | 8/2008 |
| WO | 2019190332 | A1 | 10/2019 |

OTHER PUBLICATIONS

EspaceNet Translation Zhang CN203584917 (Year: 2014).*
Communication pursuant to Article 94(3) EPC, Office Action for EP Application No. 20909220.4, European Patent Office, issued on Sep. 24, 2025, pp. 1-7.

* cited by examiner

20

NOISE REDUCTION STRUCTURE FOR VENTILATION TREATMENT DEVICE AND VENTILATION TREATMENT DEVICE

CROSS REFERENCE TO RELEVANT APPLICATIONS

This application is the national phase entry of International Application No. PCT/CN2020/125857, filed on Nov. 2, 2020, which is based upon and claims priority to Chinese Patent Application No. 201911398517X, filed on Dec. 30, 2019: the entire contents of which are incorporated herein by reference.

TECHNICAL FIELD

The present disclosure relates to the field of ventilation-treatment devices, and more particularly, to a noise reduction structure for a ventilation-treatment device and a ventilation-treatment device comprising the noise reduction structure.

BACKGROUND

In a ventilation-treatment device, the centrifugal fan is a core component. The noise generated by the operation of the centrifugal fan will be radiated into the air passage communicate with the gas inlet of the fan, and generate an intensive aerodynamic noise and is then radiated out of the device. However, most of the users of the ventilation-treatment devices are patients having the sleep apnea syndrome, and the large aerodynamic noise results in that the patients cannot use the devices comfortably.

In order to reduce the aerodynamic noise generated in the air passage, conventional ventilation-treatment devices usually employ resistance-type noise reduction (for example, filling the air passage with a sound absorbing cotton), blocking-type noise reduction (for example, configuring the air passage to have a plurality of turning points) or resistance-blocking-type noise reduction. However, those types have a limited effect of noise reduction to the noise (especially low-frequency noise), and they also bring a large difficulty in structural designing, a complicated manufacturing process, a high overall cost, and they further require a large structural space.

Therefore, it is necessary to provide a noise reducing structure that may effectively reduce the aerodynamic noise in the air passage, to improve the satisfaction of usage of the patient.

SUMMARY

An object of the present disclosure is to provide a noise reducing structure for a ventilation-treatment device and a ventilation-treatment device comprising the noise reducing structure, to solve the above problems.

In order to achieve the above objects, one aspect of the present disclosure provides a noise reducing structure for a ventilation-treatment device, wherein the noise reducing structure comprises a first micropore plate, the first micropore plate is provided with a first plate surface and a second plate surface which are opposite to each other, the first plate surface is configured for forming a first chamber, the second plate surface is for forming an air passage, to make gas inside the air passage to flow along the second plate surface, and the first micropore plate is provided with a plurality of first micro-through holes communicating the first chamber and the air passage.

Optionally, the noise reducing structure comprises a first back plate, and the first back plate is stacked at intervals on a side of the first plate surface of the first micropore plate, to form the first chamber together with the first plate surface.

Optionally, the first chamber is filled with a sound absorbing cotton.

Optionally, the noise reducing structure comprises a second micropore plate, the second micropore plate is stacked at intervals between the first micropore plate and the first back plate, and partitions the first chamber into an upper chamber close to the first micropore plate and a lower chamber close to the first back plate, and the second micropore plate is provided with a plurality of second micro-through holes communicating the upper chamber and the lower chamber.

Optionally, the upper chamber and the lower chamber are filled with a sound absorbing cotton.

Optionally, the noise reducing structure comprises a second micropore plate, the second micropore plate is stacked at intervals on a side of the second plate surface of the first micropore plate, to form the air passage together with the second plate surface, and the second micropore plate is provided with a plurality of second micro-through holes communicate with the air passage.

Optionally, the noise reducing structure comprises a second back plate, the second back plate is stacked at intervals on one side of the second micropore plate that is away from the first micropore plate, to form a second chamber between the second micropore plate and the second back plate, and the second chamber communicates with the air passage via the second micro-through holes.

Optionally, the first micropore plate and the second micropore plate are installed to circumferentially seal the air passage, and forming a gas inlet and a gas outlet which are communicate with the air passage at two opposite ends.

Optionally, the second chamber is filled with a sound absorbing cotton.

Optionally, the noise reducing structure comprises a plurality of first partition plates, the plurality of first partition plates are disposed inside the air passage and extend in a flow direction of gas inside the air passage, respectively, and the plurality of first partition plates are disposed at intervals to partition the air passage into a plurality of branch air passages.

Optionally, the noise reducing structure comprises a plurality of second partition plates, the plurality of second partition plates are disposed inside the plurality of branch air passages, respectively, the second partition plates are disposed at intervals and parallel to the first partition plates, both of the first partition plates and the second partition plates extend are disposed to from the gas inlet to the gas outlet, and an extension length of the second partition plates is less than an extension length of the first partition plates.

Another aspect of the present disclosure provides a ventilation-treatment device, wherein the ventilation-treatment device comprises the noise reducing structure stated above.

Optionally, the ventilation-treatment device comprises a ventilating tube assembly and a fan, a gas-inlet port of the ventilating tube assembly communicates with a gas outlet of the fan, and the air passage communicates with a gas inlet of the fan.

Optionally, the ventilation-treatment device comprises a housing assembly, the housing assembly comprises a cavity, and a gas inlet and a gas outlet that are communicate with the cavity, the noise reducing structure, the ventilating tube assembly and the fan are disposed inside the cavity, the air passage communicates the gas inlet of the housing assembly and the gas inlet of the fan, and a gas-outlet port of the ventilating tube assembly communicates with the gas outlet of the housing assembly.

Optionally, the housing assembly comprises a middle housing and a lower housing that form the cavity, the middle housing detachably covers a top of the lower housing, a gas-inlet end wall of the middle housing is provided with a middle-housing gas inlet communicate with the cavity, a gas-inlet end wall of the lower housing is provided with a lower-housing gas inlet communicate with the cavity, and the middle-housing gas inlet and the lower-housing gas inlet form the gas inlet of the housing assembly together.

Optionally, the ventilation-treatment device comprises a decorating assembly, the decorating assembly encircles the housing assembly, and is provided with a gas inlet and a gas outlet that correspond to the gas inlet and the gas outlet of the housing assembly, the decorating assembly comprises a filtering member, and the filtering member is provided at the gas inlet of the decorating assembly.

Optionally, a chamber is formed between the gas-inlet end wall of the middle housing and the gas-inlet end wall of the lower housing and the filtering member, a dividing plate assembly is provided inside the chamber, the dividing plate assembly partitions the chamber into at least two areas, the gas-inlet end wall of the middle housing that is located in each of the areas is provided with at least one instance of the middle-housing gas inlet, and the gas-inlet end wall of the lower housing that is located in each of the areas is provided with at least one instance of the lower-housing gas inlet.

Optionally, the dividing plate assembly partitions the chamber equally into a left area and a right area in a horizontal direction, the dividing plate assembly comprises a first splitter plate and a second splitter plate, the first splitter plate is formed protrusively on an outer side surface of the gas-inlet end wall of the middle housing and extends in a vertical direction, the second splitter plate is formed protrusively on an outer side surface of the gas-inlet end wall of the lower housing and extends in a same direction as the extension direction of the first splitter plate, the middle-housing gas inlets located in the left area and the right area are disposed symmetrically with each other, and the lower-housing gas inlets located in the left area and the right area are disposed symmetrically with each other.

By using the above technical solutions, when the noise reducing structure according to the present disclosure is applied to the ventilation-treatment device, part of the gas flow inside the air passage enters the first chamber via the first micro-through holes in the first micropore plate. When the gas flow passes through the first micro-through holes, a viscous dissipation may happen to remove part of the high-frequency noise in the gas flow. The gas flow entering the first chamber resonates with the other walls forming the first chamber to convert the low-frequency noise in the gas flow into high-frequency noise, and when the gas flow returns to the air passage via the first micro-through holes, the high-frequency noise is partially removed by the viscous dissipation. The remaining high-frequency noise in the gas flow returning to the air passage has high-frequency overlapping with the other gas flows inside the air passage and is offset. Furthermore, the gas flow returning to the air passage disturbs the other gas flows, which increases the viscous dissipation of the other gas flows when entering the first chamber via the first micro-through holes, thereby removing more high-frequency noise. Accordingly, the noise reducing structure according to the present disclosure has a wide noise-reduction frequency band, and may effectively reduce the aerodynamic noise in the air passage, to improve the satisfaction of the patient in the usage of the ventilation-treatment device. In addition, the noise reducing structure has the advantages of simple manufacturing and designing, a low cost, a small required structural space and extensive application environments.

The other characteristics and advantages of the present disclosure will be described in detail in the subsequent section of DETAILED DESCRIPTION OF THE EMBODIMENTS.

BRIEF DESCRIPTION OF THE DRAWINGS

The drawings are intended to provide a further understanding of the present disclosure, and constitute part of the description. The drawings are intended to interpret the present disclosure together with the following particular embodiments, and do not function to limit the present disclosure. In the drawings:

FIG. 61 is a schematic diagram of the fan supporting cotton provided inside the lower housing shown in FIG. 49.

DESCRIPTION OF THE REFERENCE NUMBERS

Figure 1:
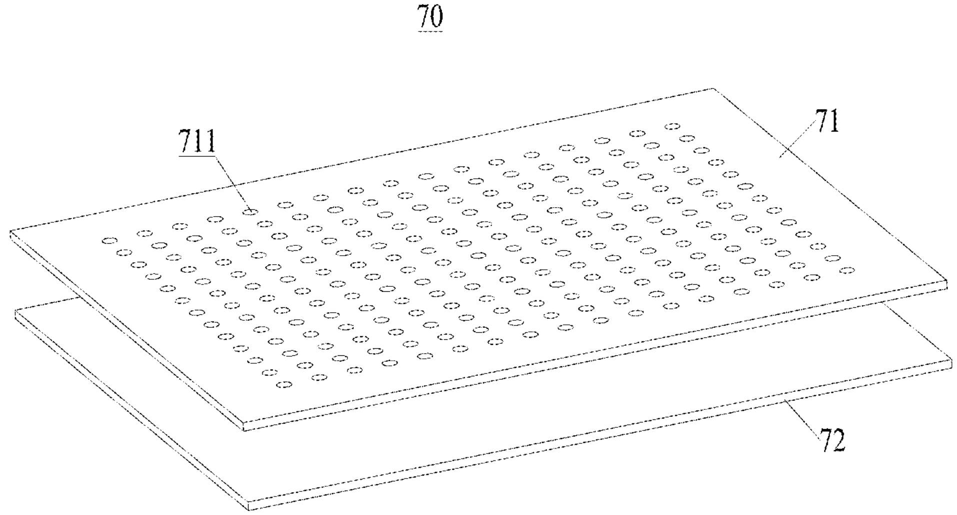
FIG. 1 is a perspective view of the first embodiment of the noise reducing structure according to the present disclosure.

10—flow guiding member, 11—tube body, 111—first tube orifice, 112—second tube orifice, 113—first lumen, 114—second lumen, 115—inner tube body, 116—outer tube body, 12—installing base, 121—round ring, 122—third positioning member, 123—connecting rib, 13—first guiding plate, 14—second guiding plate, and 15—third guiding plate;

20—ventilating tube assembly, 21—first tube piece, 210—first positioning member, 211—gas-inlet port, 212—gas-inlet cavity, 213—first gas cavity, 214—first communicating opening, 215—first annular wall, 216—second annular wall, 217—first opening, 218—first annular flange, 219—first installing part, 22—second tube piece, 220—first positioning slot, 221—gas-outlet port, 222—gas-outlet cavity, 223—second gas cavity, 224—second communicating opening, 225—third annular wall, 226—fourth annular wall, 227—second opening, 23—first collecting branch tube, 24—second collecting branch tube, 25—gas blocking member, 251—second positioning member, and 26—pressure collecting tube;

30—sealing connector, 31—first socket, 32—second socket, 33—first channel, 34—third socket, 35—fourth socket, 36—fifth socket, 37—sixth socket, 38—first sealing strip, and 39—second sealing strip;

40—fan, 41—gas-outlet channel, 42—gas outlet, 43—second annular flange, 44—gas inlet, 45—housing, and 46—gas-outlet tube;

50—connector, 51—housing, 52—second installing part, 53—third installing part, and 54—installing slot.

60—PCBA plate, 61—mainboard, 611—through hole, 612—device-status light, 613—on-off-status light, 614—Bluetooth-status light, 62—lap-joining board, 63—pressure sensor, 64—contact pin, 65—pressure-differential flow-rate sensor, 651—high-pressure input point, 652—low-pressure input point, 66—power-button touch spring, and 67—Bluetooth-key touch spring;

70—noise reducing structure, 71—first micropore plate, 711—first micro-through holes, 712—connecting pillar, 713—positioning pillar, 714—first plate surface, 715—second plate surface, 72—first back plate, 73—first chamber, 731—upper chamber, 732—lower chamber, 74—air passage, 741—gas inlet, 742—gas outlet, 743—first partition plates, 744—branch air passages, 745—second partition plates, 75—sound absorbing cotton, 751—sound-absorbing-cotton through hole, 752—sound-absorbing-cotton arc wall, 76—second micropore plate, 761—second micro-through holes, 762—connecting hole, 763—positioning slots, 764—snap-fitting slot, and 77—second chamber;

80—housing assembly, 81—upper housing, 811—operation panel, 8111—power button, 8112—Bluetooth key, 8113—light transmitting ring, 8114—upper-housing clipping slot, 8115—upper-housing positioning slot, 8116—upper-housing fixing hole, 82—middle housing, 820—flange, 821—middle-housing noise reducing cotton, 8211—middle-housing-noise-reducing-cotton arc wall, 822—middle-housing connecting hole, 823—middle-housing supporting part, 824—middle-housing fixing hole, 825—sound-absorbing-cotton installing area, 8251—sound-absorbing-cotton inserting part, 826—fan installing area, 827—middle-housing noise-reducing-cotton installing area, 8271—middle-housing-noise-reducing-cotton inserting part, 828—middle-housing limiting parts, 829—middle-housing buckle, 83—lower housing, 831—gas-inlet chamber, 8311—gas-inlet noise reducing cotton, 8312—electric assembly, 832—fan chamber, 8321—fan supporting cotton, 8322—first side wall, 8323—installing opening, 8324—annular limiting rib, 8325—bottom limiting rib, 833—gas-outlet chamber, 834—sealer, 835—power-supply-socket assembly, 836—sealer installing slot, 837—lower-housing fixing hole, 838—power-supply-socket installing slot, 839—lower-housing clipping slot, 84—sealing ring, 85—gas inlet, 851—middle-housing gas inlet, 8511—inclined elongate through hole, 8512—circular through hole, 852—lower-housing gas inlet, 853—first splitter plate, 854—second splitter plate, 86—gas outlet, 87—base, 871—slide-proof pad, 872—slide-proof-gasket installing slot, and 88—bolt; and

90—decorating assembly, 91—side decorating member, 911—first buckle, 912—second buckle, 913—positioning part, 914—supporting part, 92—gas-inlet decorating member, 93—gas-outlet decorating member, 94—filtering cotton, 95—filtering-cotton cover, 951—through hole, and 952—protrusions.

DETAILED DESCRIPTION OF THE EMBODIMENTS

The particular embodiments of the present disclosure will be described in detail below with reference to the drawings. It should be understood that the particular embodiments described herein are merely intended to describe and interpret the present disclosure, and are not intended to limit the present disclosure.

In the present disclosure, unless stated otherwise, the used words of orientation, such as "upper", "lower", "top" and "bottom" refer to the orientations in the installation and usage states, and "inner" and "outer" refer to the interior and the exterior with respect to the contours of the components themselves.

The first aspect of the present disclosure provides a noise reducing structure for a ventilation-treatment device, wherein the noise reducing structure 70 comprises a first micropore plate 71, the first micropore plate 71 has a first plate surface 714 and a second plate surface 715 which are opposite to each other, the first plate surface 714 is configured for forming a first chamber 73, the second plate surface

Figure 2:
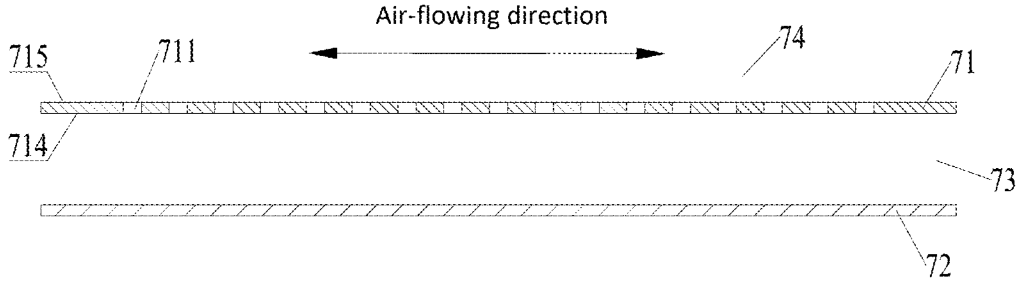
FIG. 2 is a cross-sectional view of the noise reducing structure in FIG. 1.

715 is configured for forming an air passage 74, to make the gas inside the air passage 74 to flow along the second plate surface 715, and the first micropore plate 71 is provided with a plurality of first micro-through holes 711 communicating the first chamber 73 and the air passage 74 (refer to FIGS. 1 and 2).

By using the above technical solutions, when the noise reducing structure 70 according to the present disclosure is applied to the ventilation-treatment device, part of the gas flow inside the air passage 74 enters the first chamber 73 via the first micro-through holes 711 in the first micropore plate 71. When the gas flow passes through the first micro-through holes 711, a viscous dissipation may happen to remove part of the high-frequency noise in the gas flow. The gas flow entering the first chamber 73 resonates with the other walls (for example, the first back plate 72 described below) forming the first chamber 73 to convert the low-frequency noise in the gas flow into high-frequency noise, and when the gas flow returns to the air passage 74 via the first micro-through holes 711, the high-frequency noise is partially removed by the viscous dissipation. The remaining high-frequency noise in the gas flow returning to the air passage 74 has high-frequency overlapping with the other gas flows inside the air passage 74 and is offset. Furthermore, the gas flow returning to the air passage 74 disturbs the other gas flows, which increases the viscous dissipation of the other gas flows when entering the first chamber 73 via the first micro-through holes 711, thereby removing more high-frequency noise. Accordingly, the noise reducing structure 70 according to the present disclosure has a wide noise-reduction frequency band, and may effectively reduce the aerodynamic noise in the air passage 74, to improve the satisfaction of the patient in the usage of the ventilation-treatment device. In addition, the noise reducing structure 70 has the advantages of simple manufacturing and designing, a low cost, a small required structural space and extensive application environments.

In the present disclosure, as shown in FIGS. 1 and 2, the noise reducing structure 70 may further comprise a first back plate 72, and the first back plate 72 is stacked at intervals on the side of the first plate surface 714 of the first micropore plate 71, to form the first chamber 73 together with the first plate surface 714.

Figure 3:
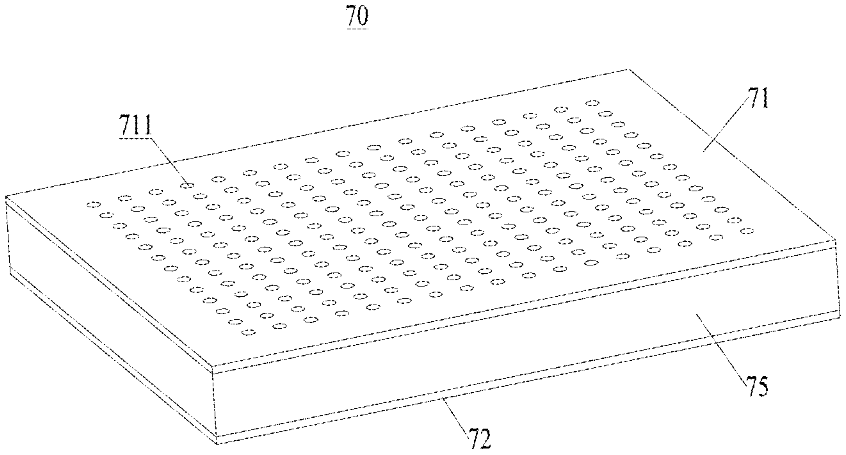
FIG. 3 is a perspective view of the second embodiment of the noise reducing structure according to the present disclosure.
Figure 4:
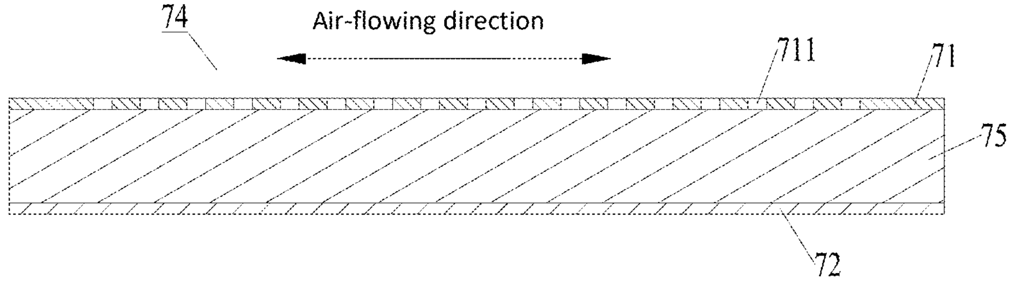
FIG. 4 is a cross-sectional view of the noise reducing structure in FIG.

In order to further improve the effect of noise reduction, according to an embodiment of the present disclosure, as shown in FIGS. 3 and 4, the first chamber 73 may be filled with a sound absorbing cotton 75.

Figure 5:
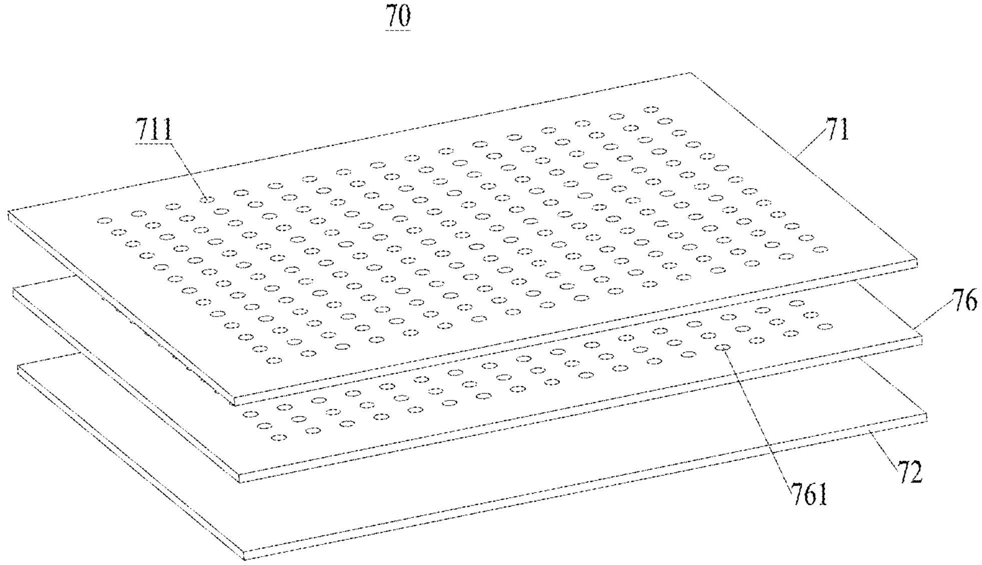
FIG. 5 is a perspective view of the third embodiment of the noise reducing structure according to the present disclosure.
Figure 6:
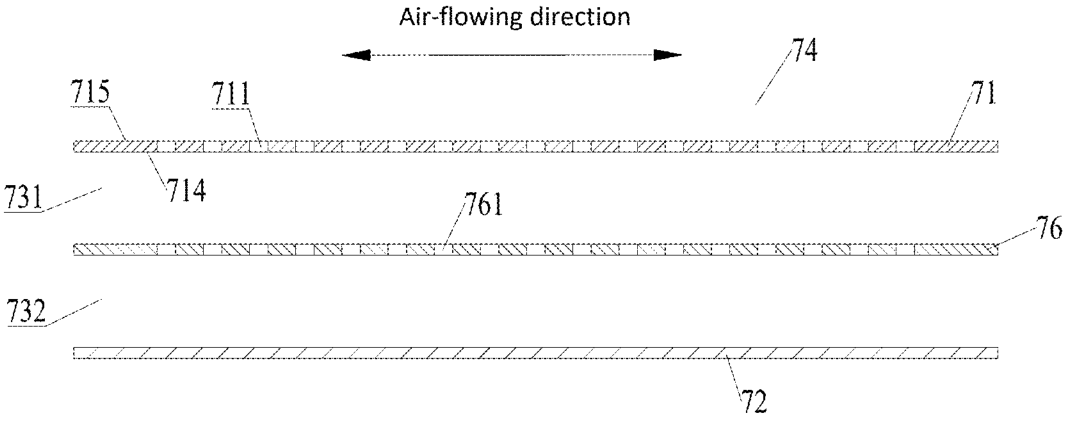
FIG. 6 is a cross-sectional view of the noise reducing structure in FIG. 5.
Figure 7:
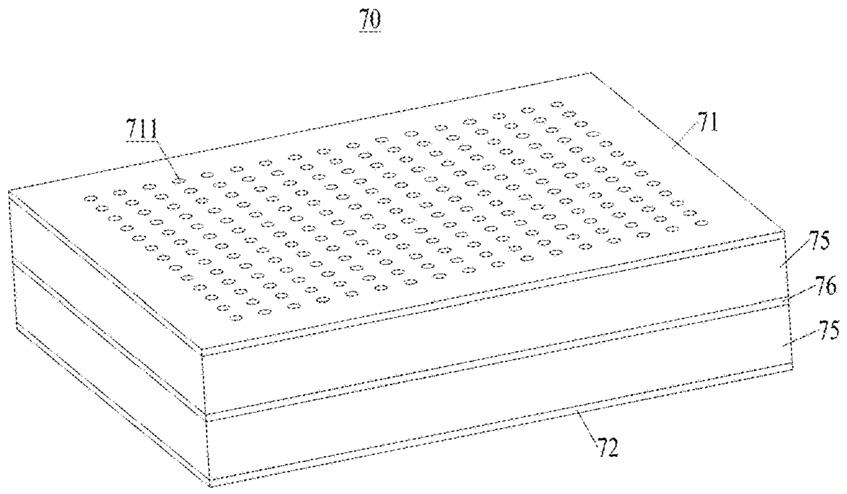
FIG. 7 is a perspective view of the fourth embodiment of the noise reducing structure according to the present disclosure.
Figure 8:
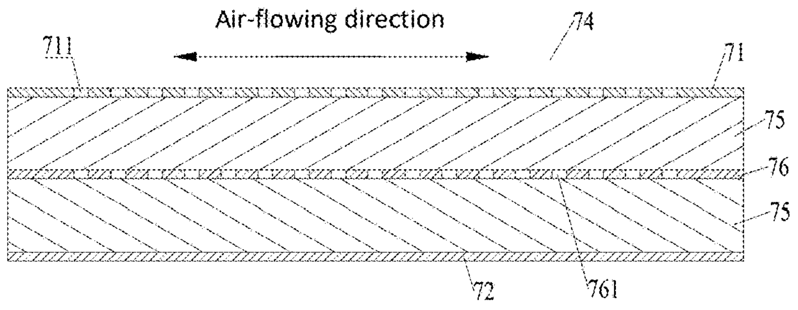
FIG. 8 is a cross-sectional view of the noise reducing structure in FIG. 7.

According to another embodiment of the present disclosure, as shown in FIGS. 5 and 6, the noise reducing structure 70 may include a second micropore plate 76, the second micropore plate 76 is stacked at intervals between the first micropore plate 71 and the first back plate 72, and partitions the first chamber 73 into an upper chamber 731 close to the first micropore plate 71 and a lower chamber 732 close to the first back plate 72 (the upper and the lower used here refer to the orientations shown in FIG. 6, and are not particular), and the second micropore plate 76 is provided with a plurality of second micro-through holes 761 communicating the upper chamber 731 and the lower chamber 732. Accordingly, in usage, part of the gas inside the air passage 74 may enter the upper chamber 731 via the first micro-through holes 711 in the first micropore plate 71, and subsequently enter the lower chamber 732 via the second micro-through holes 761 in the second micropore plate 76 to resonate with the first back plate 72. Due to the gas sequentially passes through the first micro-through holes 711 and the second micro-through holes 761, two times of viscous dissipation happen to remove more high-frequency noise. Moreover, when the gas entering the lower chamber 732 returns to the air passage 74 via the second micro-through holes 761 and the first micro-through holes 711, two times of viscous dissipation may also happen to remove more high-frequency noise, thereby reaching a better effect of noise reduction. Optionally, in the present embodiment, in order to further improve the effect of noise reduction, as shown in FIGS. 7 and 8, the upper chamber 731 and the lower chamber 732 may be filled with a sound absorbing cotton 75. Certainly, in another embodiment, the noise reducing structure 70 may include a plurality of second micropore plates 76 that are stacked at intervals with each other.

In the above embodiment, the combination of the first micropore plate 71, the first chamber 73 and the first back plate 72 forms the air passage 74 as a unit. Particularly, in an embodiment, the air passage 74 may be completely formed by the unit. For example, the unit may be configured as a cylindrical shape (in other words, all of the first micropore plate 71, the first chamber 73 and the first back plate 72 are cylindrical shapes), and the cylindrical cavity in the cylinder is the air passage 74. In another embodiment, the unit may be used to form part of the air passage 74. For example, the air passage 74 is formed by the unit together with another component, or the air passage 74 is formed by a plurality of the units.

Particularly, referring to the embodiment shown in FIGS. 9-12, the air passage 74 is formed by two of the units, the noise reducing structure 70 further comprises a second micropore plate 76 and a second back plate, the second micropore plate 76 is stacked at intervals on the side of the second plate surface 715 of the first micropore plate 71, to form the air passage 74 together with the second plate surface 715, and the gas inside the air passage 74 may flow along the plate surface of the second micropore plate 76 that faces the first micropore plate 71; and the second back plate is stacked at intervals on the one side of the second micropore plate 76 that is away from the first micropore plate 71, to form a second chamber 77 between the second micropore plate 76 and the second back plate, and the second chamber 77 communicates with the air passage 74 via the plurality of second micro-through holes 761 in the second micropore plate 76.

In order to further improve the effect of noise reduction, the second chamber 77 may be filled with a sound absorbing cotton 75.

It should be noted that FIGS. 9-12 do not show the first back plate 72 and the second back plate, and the noise reducing structure 70 shown in FIGS. 9-12 is a specific structure that is applied to the ventilation-treatment device described below. In such a ventilation-treatment device, the first back plate 72 and the second back plate are not required to be independently disposed, and other components in the ventilation-treatment device play the roles as the first back plate 72 and the second back plate.

It should be noted that the micropore plate according to the present disclosure (i.e., the first micropore plate 71 and the second micropore plate 76) refers to a plate piece that is provided with a plurality of micro-through holes therein (for example, the first micro-through holes 711 in the first micropore plate 71 and the second micro-through holes 761 in the second micropore plate 76). The so-called micro-through holes are named with respect to the plate thickness, wherein the diameters of the micro-through holes are less than or equal to the plate thicknesses. The axial direction of the micro-through holes is perpendicular to the plane where the plate piece is located. The micro-through holes may be provided with any suitable cross-sectional shapes, such as a square, a circle and an ellipse. The hole diameter of the micro-through holes may be configured to be constant (for example, the first micro-through holes 711 shown in FIG. 12) or gradually change (for example, the second micro-through holes 761 shown in FIG. 12) in the axial direction. The back plate according to the present disclosure (i.e., the first back plate 72 and the second back plate) refers to a plate piece that is not provided with a hole therein. In addition, the chambers according to the present disclosure (i.e., the first chamber 73 and the second chamber 77) are preferably sealed, the chambers may be sealed by installing the micropore plates and the back plates, and may also be sealed by means of other components or structures. For example, the noise reducing structure 70 may include a side plate disposed between the micropore plate and the back plate, and the two ends of the side plate are connected to the micropore plate and the back plate. Alternatively, the noise reducing structure 70 may be disposed inside a housing which is provided with the air passage 74, the chamber is sealed by means of the housing (refer to the description below on the ventilation-treatment device), and the air passage 74 communicates with the chamber via the micro-through holes. The micropore plates and the back plates according to the present disclosure may be provided with any suitable shapes and structures, which are not limited to those shown in the drawings.

Figure 9:
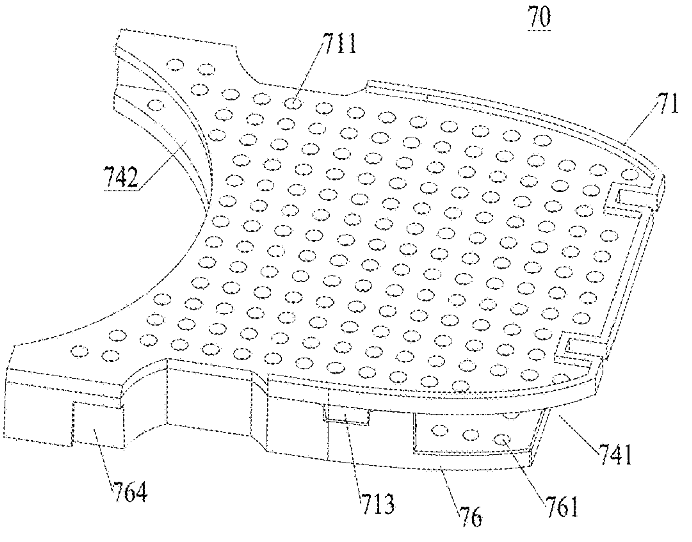
FIG. 9 is a perspective view of the fifth embodiment of the noise reducing structure according to the present disclosure, wherein merely the first micropore plate and the second micropore plate are shown.

According to an embodiment of the present disclosure, the first micropore plate 71 and the second micropore plate 76 may be installed to circumferentially seal the air passage 74, and form a gas inlet 741 and a gas outlet 742 that are communicate with the air passage 74 at the two opposite ends. Particularly, for example, as shown in FIGS. 9 and 10, both of the first micropore plate 71 and the second micropore plate 76 are provided with a side wall that extends toward each other and is configured for the installation, the first micropore plate 71 and the second micropore plate 76 are disposed with a connecting pillar 712 and a connecting hole 762, a positioning pillar 713 and a positioning slot 763 that are mutually connected, respectively, and the left end and the right end of the noise reducing structure 70 are completely opened to form a gas outlet 742 and a gas inlet 741 with a large area, respectively.

Figure 10:
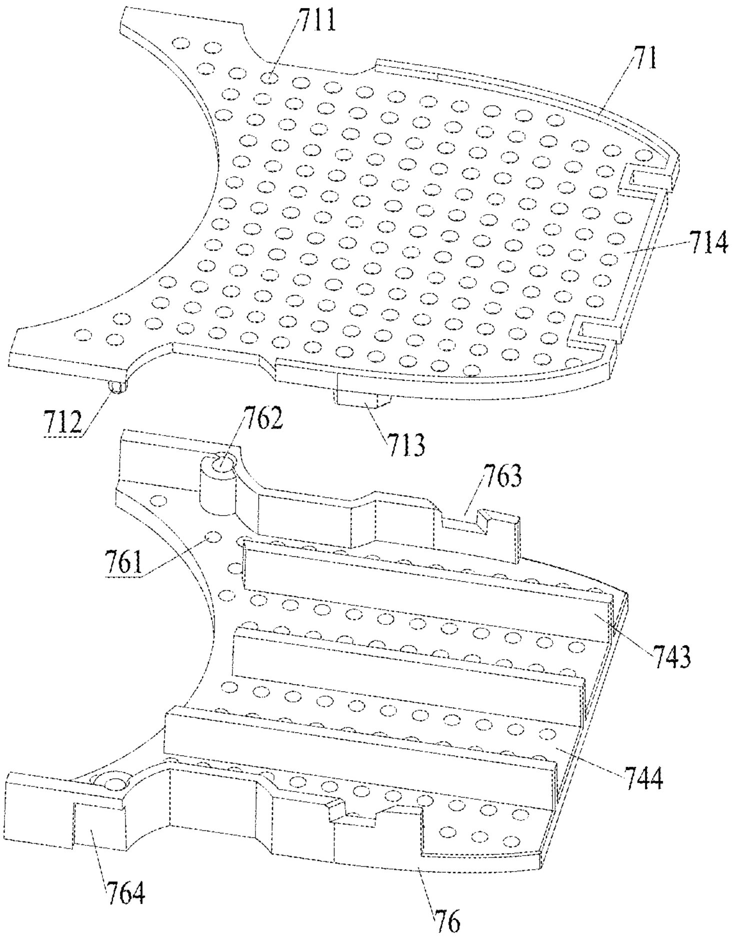
FIG. 10 is an explosive view of the noise reducing structure in FIG. 9.

In the present disclosure, as shown in FIG. 10, the noise reducing structure 70 may further include a plurality of first partition plates 743, the plurality of first partition plates 743 are disposed inside the air passage 74 and extend in the flow direction of the gas inside the air passage 74, and the plurality of first partition plates 743 are disposed at intervals to partition the air passage 74 into a plurality of branch air passages 744. In this manner, the gas flows in the air passage 74 may be divided, to reduce the noise.

Figure 11:
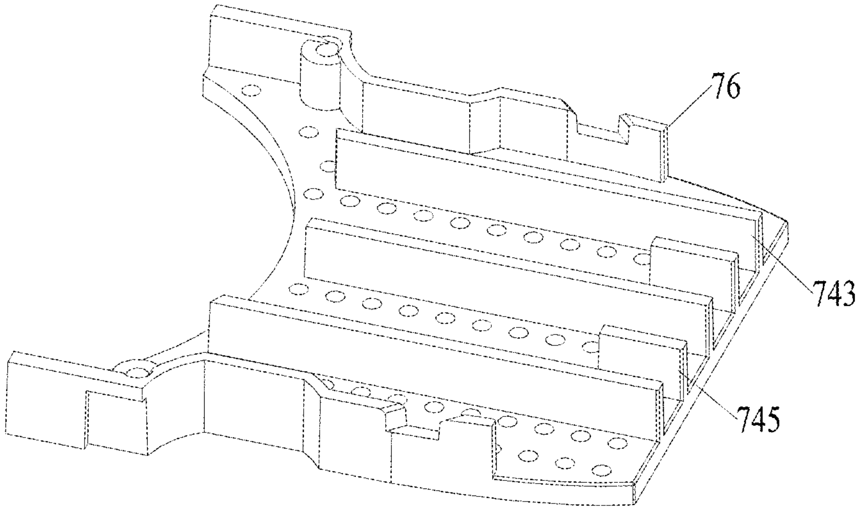
FIG. 11 is a schematic structural diagram of another embodiment of the second micropore plate in FIG. 10.
Figure 12:
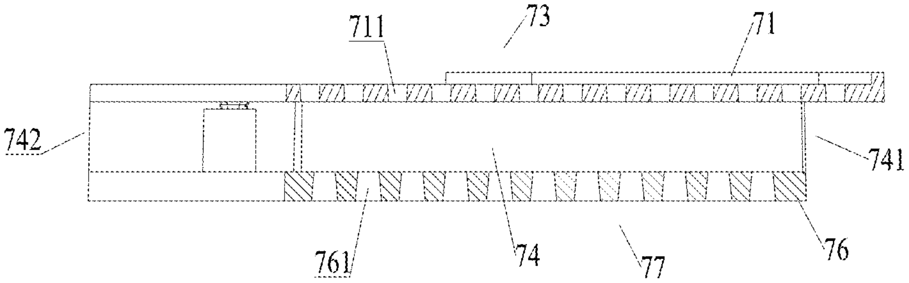
FIG. 12 is a cross-sectional view of the noise reducing structure in FIG. 9.

Optionally, as shown in FIG. 11, the noise reducing structure 70 may further include a plurality of second partition plates 745, the plurality of second partition plates 745 are disposed inside the plurality of branch air passages 744 (in other words, the second partition plates 745 and the branch air passages 744 correspond one to one), the second partition plates 745 are disposed at intervals and parallel to first partition plates 743 (it may be understood that a second partition plate 745 partitions a branch air passage 744 into two smaller branch air passages), both of the first partition plates 743 and the second partition plates 745 are disposed to extend from the gas inlet 741 to the gas outlet 742, and the extension length of the second partition plates 745 is less than the extension length of the first partition plates 743.

When the rotational speed of the fan of the ventilation-treatment device is fluctuating to generate dynamic noise, and the eddy current at the gas inlet 741 of the air passage 74 is serious. By using the above configuration, disposing the second partition plates 745 inside each of the branch air passages 744, to further divide the gas flows in order to reduce the eddy current at the gas inlet 741. Furthermore, due to the second partition plates 745 are short, the gas resistance inside the air passage 74 may not greatly increase.

The lengths of the first partition plates 743 and the second partition plates 745 may be determined according to practical situations. In the embodiment of the noise reducing structure shown in FIGS. 9-12 of the present disclosure, preferably, the length of the second partition plates 745 is ⅙-¼ of the length of the first partition plates 743, and more preferably, ⅕. That may ensure a low gas resistance in the air passage 74 while ensuring the effect of gas-flow dividing.

In addition, the fan of the ventilation-treatment device usually generates a large vibration in operation, and the vibration is transmitted outwardly via the other components of the device to generate noise. In order to provide an excellent stability and an excellent effect of sound muting to the device, it is required to perform damping and denoising to the fan.

In order to achieve the above objects, the second aspect of the present disclosure provides a fan installation structure. The fan installation structure includes a fan 40, a fan installing cavity and walls for forming the fan installing cavity. The fan 40 is installed inside the fan installing cavity. The fan 40 includes a housing 45. Spacings exist between all of the outer surfaces of the housing 45 and the walls; in other words, the fan 40 is suspend inside the fan installing cavity.

It should be noted that, in order to prevent that the fan 40 displaces excessively inside the fan installing cavity to result in irrecoverable inclining, and cause a failure, the spacings should not be too large, as long as it may be ensured that the fan 40 does not contact the walls. For example, the spacings may be 2 mm-20 mm.

In the fan installation structure according to the present disclosure, by making spacings between all of the outer surfaces of the housing 45 of the fan 40 and the walls of the fan installing cavity, the fan 40 may be separated from the walls, which prevents the vibration of the fan 40 from being transmitted to the walls and transmitted outwardly from the walls to generate noise. When the fan installation structure according to the present disclosure is applied to the ventilation-treatment device, the operation noise of the ventilation-treatment device may be effectively reduced.

Figure 19:
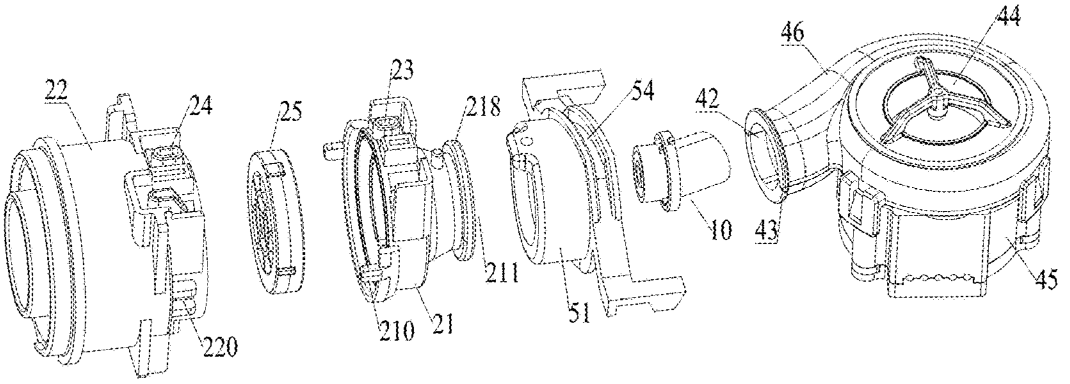
FIG. 19 is an explosive view of FIG. 18.

In the present disclosure, as shown in FIG. 19, the housing 45 is preferably a cylindrical shape, the fan 40 further includes a gas-outlet tube 46 extending outwardly from the periphery of the housing 45, the lumen of the gas-outlet tube 46 is formed as a gas-outlet channel 41, a gas inlet 44 is disposed at the top of the housing 45, and a gas outlet 42 of the fan 40 is formed at the end of the gas-outlet tube 46 that is away from the housing 45. It may be understood that the axial direction of the gas-outlet channel 41 is perpendicular to the axial direction of the housing 45.

In order to fix the fan 40 inside the fan installing cavity, the walls may include a first side wall 8322 located on the side of the gas-outlet tube of the fan 40, the first side wall 8322 is provided with an installing opening 8323 (refer to FIG. 49), and the gas-outlet tube 46 is installed at the installing opening 8323. In other words, the fan 40 is fixed and suspended inside the fan installing cavity by using the gas-outlet tube 46.

The gas-outlet tube 46 may directly support and be fixed at the installing opening 8323, and may also be installed at the installing opening 8323 by using a connector 50.

In the above embodiment, the connector 50 is preferably an elastic member (for example, a silica-gel member). In this way, the connector 50 may also play a buffer role while connecting to the gas-outlet tube 46, to reduce the transmission of the vibration of the gas-outlet tube 46 toward the first side wall 8322.

In the present disclosure, the connector 50 may have any suitable structure, as long as the gas-outlet tube 46 may be fixed at the installing opening 8323 and the smooth gas exiting of the gas-outlet tube 46 may be ensured.

Figure 20:
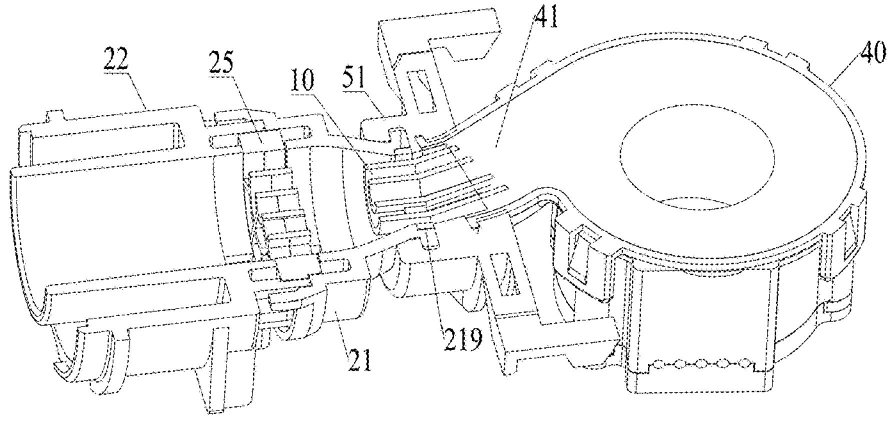
FIG. 20 is a transversely sectional view of FIG. 18.
Figure 21:
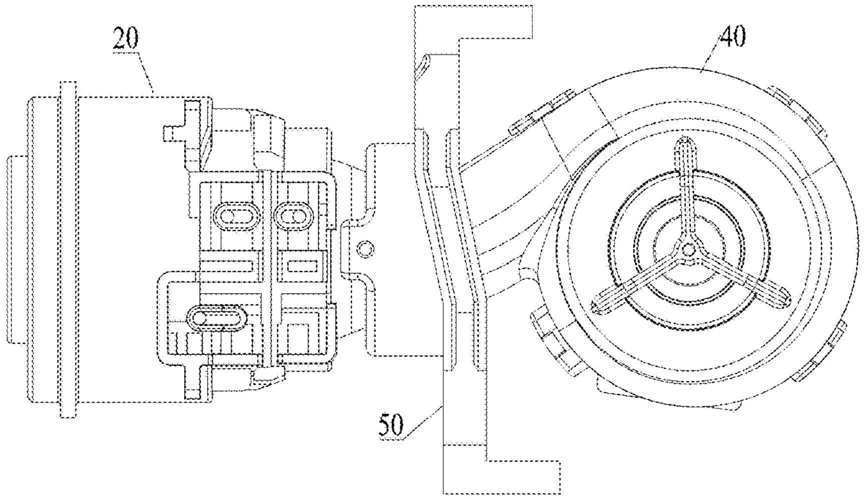
FIG. 21 is a top view of FIG. 18.

Particularly, according to an embodiment of the present disclosure, as shown in FIGS. 19 and 20, the connector 50 includes a communicating cavity which two ends are openings and a housing 51 for forming the communicating cavity, the gas-outlet end of the gas-outlet tube 46 is inserted into the communicating cavity via one of the openings and enables the gas outlet 42 to be communicate with the other opening via the communicating cavity, and an installing slot 54 for peripheral embedding of the installing opening 8323 is disposed on the outer wall surface of the housing 51. It may be understood that, in another embodiment, the housing 51 may also be connected to the periphery of the installing opening 8323 or the first side wall 8322 by using another structure.

In order to further improve the reliability of the installation of the gas-outlet tube 46, the gas-outlet end of the gas-outlet tube 46 may be connected inside the communicating cavity by using a connecting structure.

Particularly, according to an embodiment of the present disclosure, the connecting structure may include a flange and a groove that match to each other. The flange is disposed on one of the peripheral surface of the gas-outlet end of the gas-outlet tube 46 and the inner-wall surface of the housing 51, and the groove is disposed on the other of the peripheral surface of the gas-outlet end of the gas-outlet tube 46 and the inner-wall surface of the housing 51.

Figure 22:
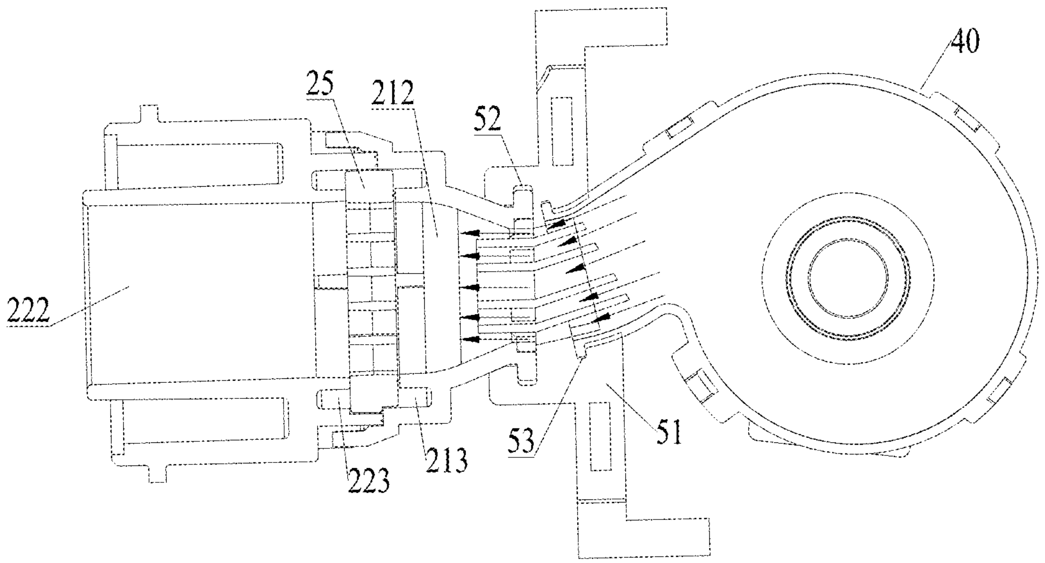
FIG. 22 is a transversely sectional view of FIG. 21.

For example, as shown in FIGS. 19 and 22, the connecting structure includes a second annular flange 43 surrounding the peripheral surface of the gas-outlet end of the gas-outlet tube 46 and an annular groove disposed on the inner-wall surface of the housing 51 and for embedding of the second annular flange 43.

In order to further improve the effect of noise reduction, a sound absorbing cotton may be disposed inside the spacing between the periphery of the fan 40 and the walls. The sound absorbing cotton absorbs the vibration of the fan 40, and may support and fix the fan 40 to a certain extent.

Particularly, the walls may include a top wall located above the fan 40, a bottom wall located below the fan 40 and a second side wall located on the side opposite to the gas-outlet tube of the fan 40, and the fan installation structure includes a top sound absorbing cotton between the top wall and the top surface of the housing 45, a bottom sound absorbing cotton between the bottom wall and the bottom surface of the housing 45 and a side sound absorbing cotton between the second side wall and the corresponding side surface of the housing 45.

Figure 59:
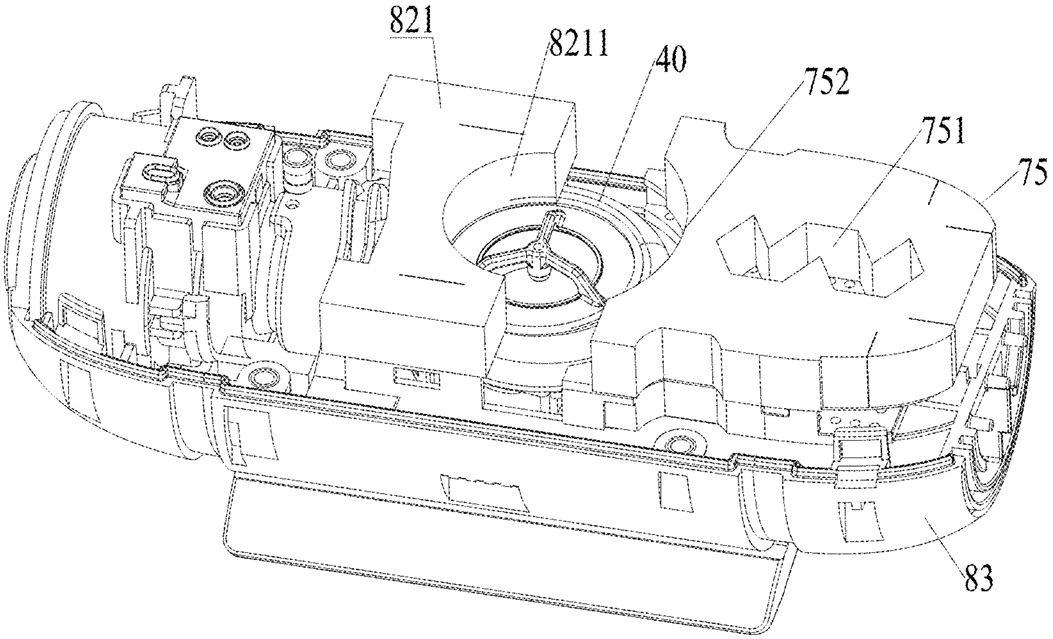
FIG. 59 is a schematic structural diagram of the ventilating device in FIG. 38 when the middle housing and the parts thereabove are removed.
Figure 60:
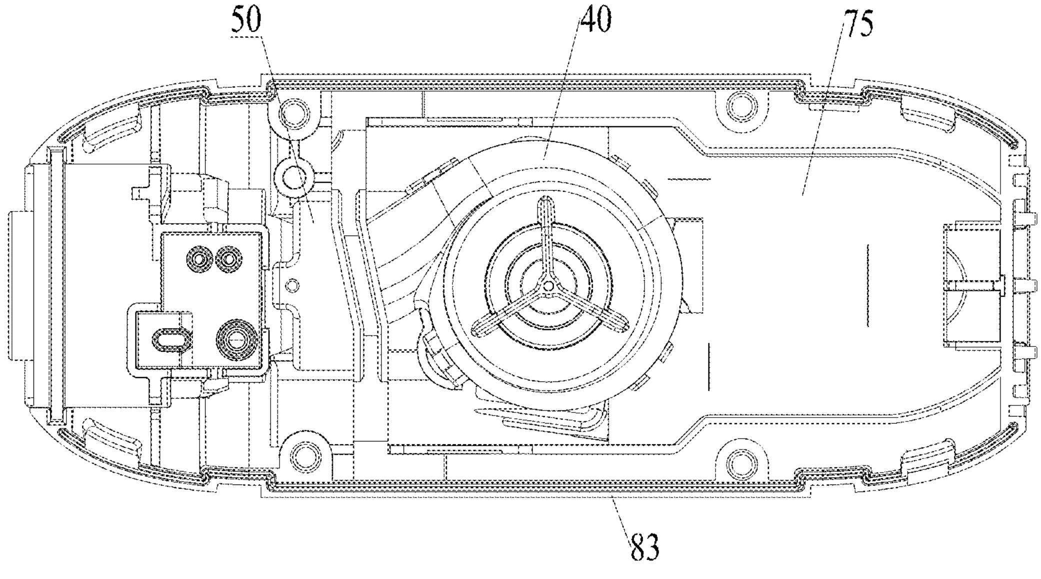
Figure 61:
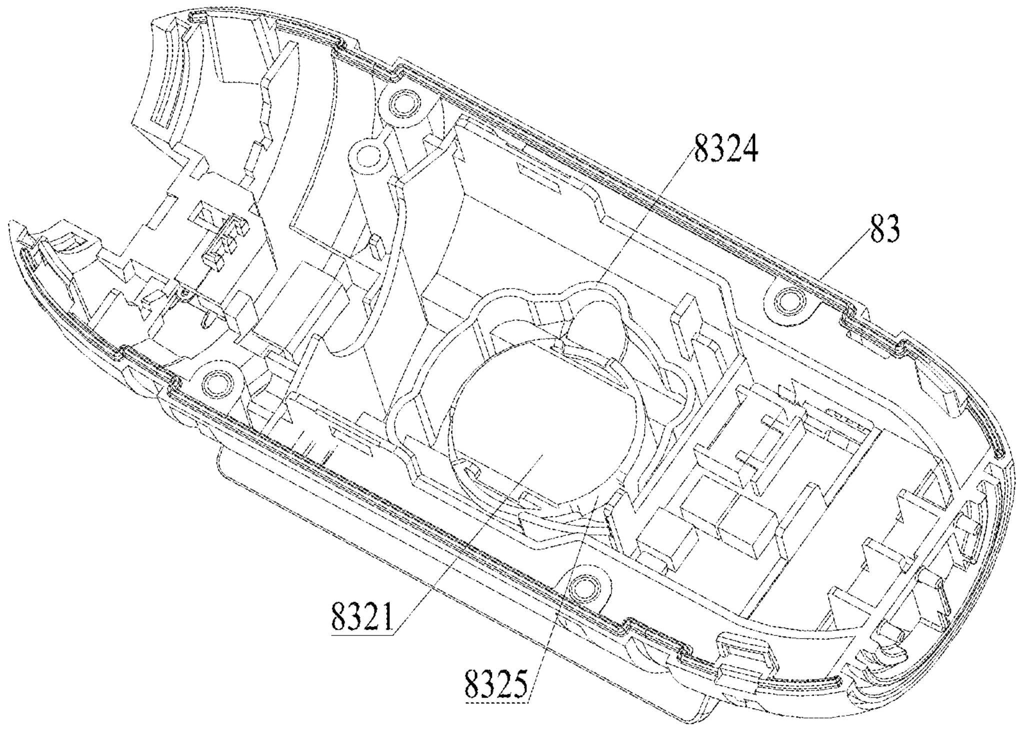
FIG. 61 is a top view of FIG. 59, wherein the top sound absorbing cotton is removed.

The top sound absorbing cotton preferably does not block the gas inlet 44 of the fan 40 (refer to FIG. 59). The side of the side sound absorbing cotton that is close to the housing 45 preferably matches with the contour of the corresponding side surface of the housing 45. For example, when the housing 45 is a cylindrical shape, the side of the side sound absorbing cotton that is close to the housing 45 is substantially circular-arc-shaped (refer to FIG. 60).

In the present disclosure, in order to prevent the case of falling or other accidents happens, the fan 40 displaces excessively and makes the gas-outlet tube 46 disengage from the connector 50 or irrecoverably incline, and cause a failure, the walls may include a top limiting component extending downwardly from the lower surface of the top wall, wherein a gap exists between the bottom surface of the top limiting component and the top surface of the housing 45. The walls may include a bottom limiting component extending upwardly from the upper surface of the bottom wall, wherein a gap exists between the top surface of the bottom limiting component and the bottom surface of the housing 45. A horizontal limiting component for limiting the housing 45 to prevent horizontal movement of the housing 45 may be disposed inside the fan installing cavity.

Figure 14:
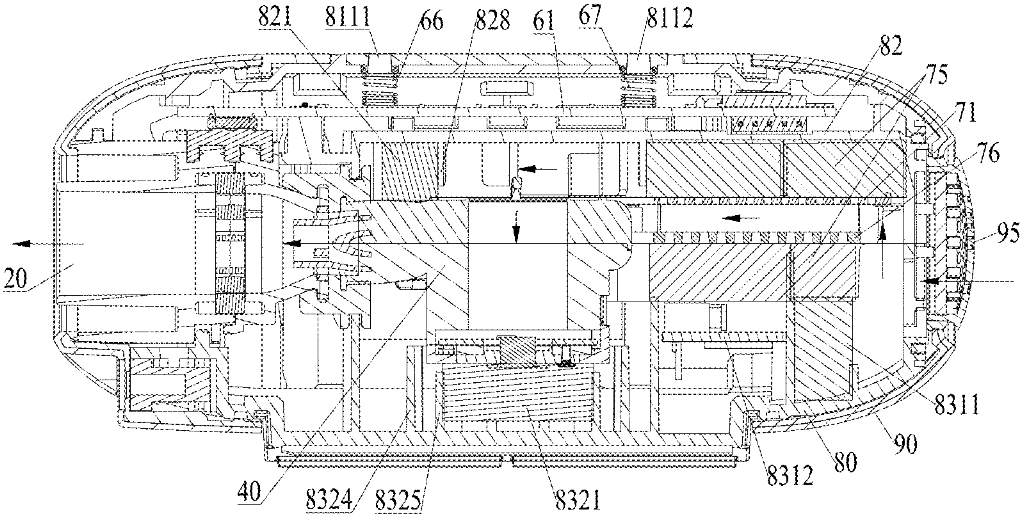
FIG. 14 is a transversely sectional view of the ventilating device in FIG. 13.
Figure 48:
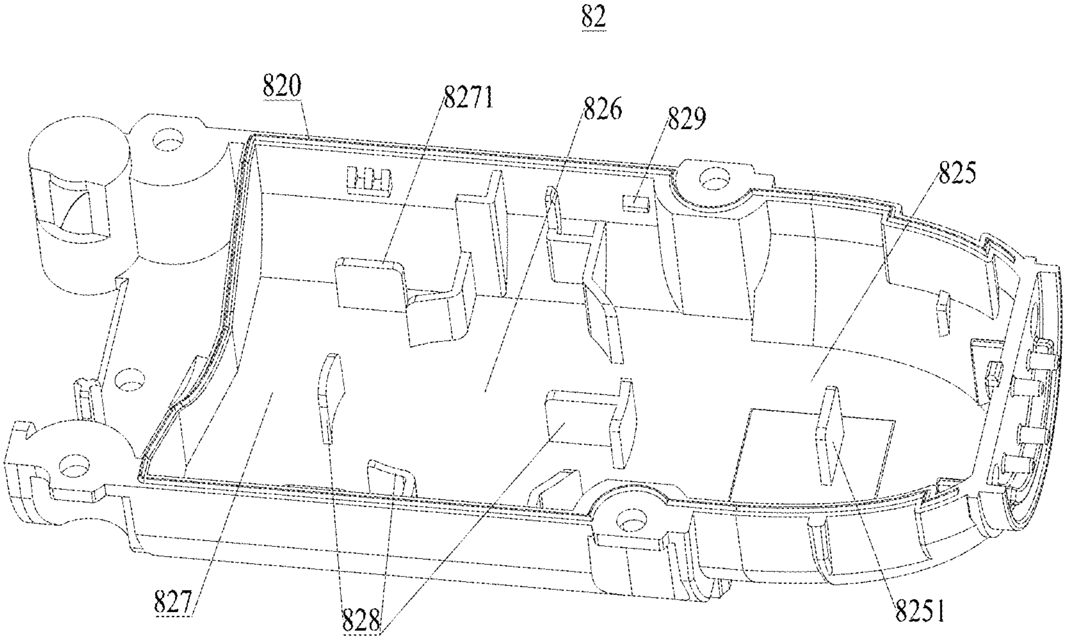
FIG. 48 is a perspective view of another angle of the middle housing in FIG. 47.

Regarding the top limiting component, particularly, for example, as shown in FIGS. 14 and 48, when the fan installation structure is applied to the ventilation-treatment device, the top wall is formed by part of the middle housing 82 of the ventilation-treatment device, and the top limiting component may include a plurality of middle-housing limiting parts 828 that are mutually disposed at intervals. When falling or other accidents happens, the top limiting component may prevent the fan 40 from upwardly displacing excessively to cause the gas-outlet tube 46 to disengage from the connector 50 or irrecoverably incline.

Figure 49:
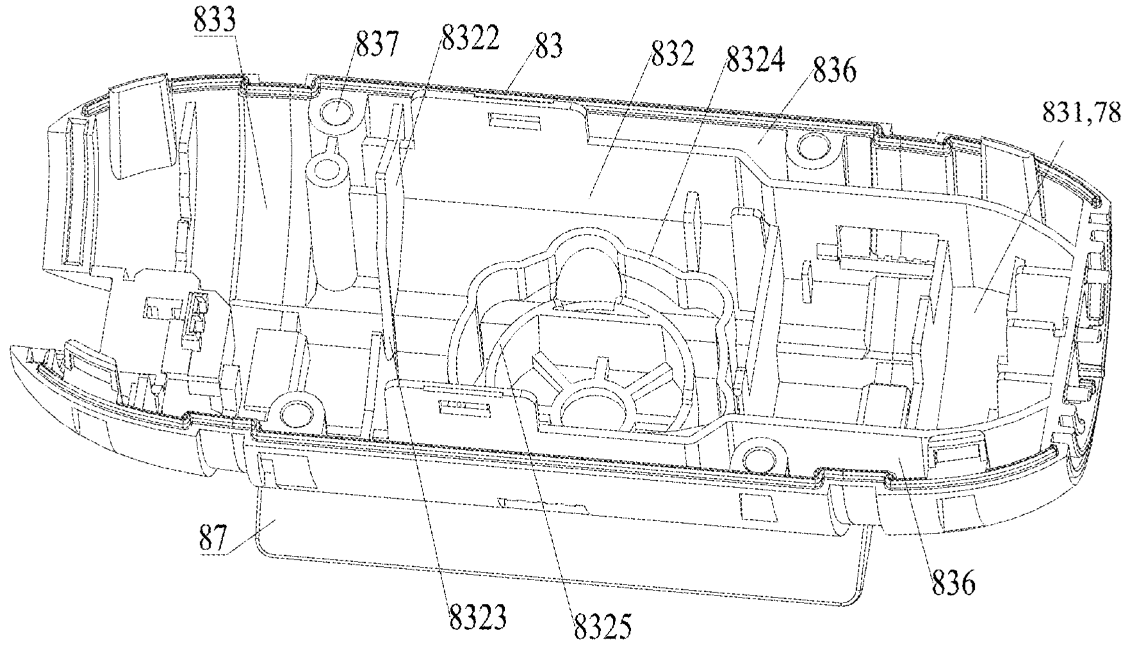
FIG. 49 is a perspective view of the lower housing in FIG. 15.

Regarding the bottom limiting component, particularly, for example, as shown in FIGS. 14 and 49, when the fan installation structure is applied to the ventilation-treatment device, the bottom wall is formed by part of the lower housing 83 of the ventilation-treatment device, and the bottom limiting component may include an annular bottom limiting rib 8325. When falling or other accidents happens, the bottom limiting component may prevent the fan 40 from downwardly displacing excessively to cause the gas-outlet tube 46 to disengage from the connector 50 or irrecoverably incline.

Regarding the horizontal limiting component, for example, as shown in FIG. 49, the horizontal limiting component may include an annular limiting rib 8324 that is connected to the walls and encircles the periphery of the housing 45, and the annular limiting rib 8324 is provided with a contour that matches with the peripheral contour of the housing 45. It should be noted that, when falling or other accidents happens, the annular limiting rib 8324 and the connector 50 may reduce the impact, to prevent the fan 40 from displacing excessively to disengage from the connector 50 or irrecoverably incline, and cause a failure.

Optionally, for example, as shown in FIG. 14, when the gas-outlet tube 46 is located at an upper position in the axial direction of the housing 45, the annular limiting rib 8324 may be configured to extend upwardly from the bottom wall. When the gas-outlet tube 46 is located at an upper position in the axial direction of the housing 45, the annular limiting rib 8324 may be configured to extend downwardly from the top wall.

It should be noted that, when the fan installation structure according to the present disclosure is applied to the ventilation-treatment device, the walls for forming the fan installing cavity may be partially or totally formed by other components (for example, the housing assembly 80 described below) of the ventilation-treatment device. That may enable the ventilation-treatment device to have compact and elaborate overall design and layout, has a small influence on the design of the complete machine and good safety and reliability, and has a very effective function of damping and denoising.

The third aspect of the present disclosure provides a ventilation-treatment device, wherein the ventilation-treatment device includes the noise reducing structure 70 stated above and/or a fan installation structure.

The ventilation-treatment device may be a breathing machine, an oxygen treatment machine and so on. The ventilation-treatment device may include a patient interface device, a ventilating tube line and a ventilating device. One end of the ventilating tube line is connected to the patient interface device, and the other end of the ventilating tube line is connected to the ventilating device. The noise reducing structure 70 is disposed in the ventilating device. The patient interface device may be a breathing mask, a nasal oxygen tube, a nasal mask, a nasal plug and so on. The ventilating tube line is configured to deliver the gas discharged by the ventilating device to the patient interface device for the patient to inhale.

The ventilating device according to an embodiment of the present disclosure will be described in detail below with reference to FIGS. 13-61.

Referring to FIGS. 18-25, the ventilating device includes a flow guiding member 10, a ventilating tube assembly 20, a gas blocking member 25 and a fan 40. The ventilating tube assembly 20 includes a ventilation cavity, and a gas-inlet port 211 and a gas-outlet port 221 that are communicate with the ventilation cavity. The gas blocking member 25 is disposed inside the ventilation cavity, and partitions the ventilation cavity in its axial direction into a gas-inlet cavity 212 close to the gas-inlet port 211 and a gas-outlet cavity 222 close to the gas-outlet port 221. The ventilating tube assembly 20 further includes a first collecting branch tube 23 communicate with the gas-inlet cavity 212 and a second collecting branch tube 24 communicate with the gas-outlet cavity 222. The fan 40 includes a gas inlet 44, a gas-outlet channel 41 and a gas outlet 42 communicate with the gas-outlet channel 41. The fan 40 is connected to the ventilating tube assembly 20 and causes the gas outlet 42 to be communicate with the gas-inlet port 211. The flow guiding member 10 is disposed inside a communicating channel of the gas outlet 42 and the gas-inlet port 211, whereby the gas flow from the gas-outlet channel 41 is guided by the flow guiding member 10 and subsequently enters the gas-inlet cavity 212 in the axial direction of the ventilation cavity.

Figure 28:
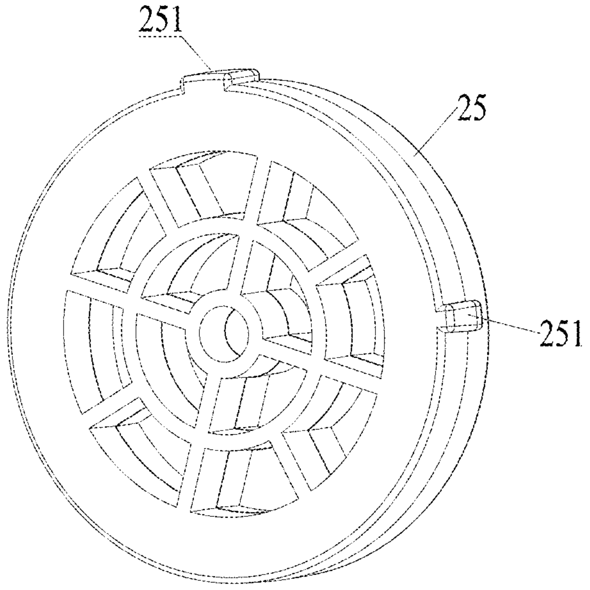
FIG. 28 is a perspective view of the gas blocking member in FIG. 19.
Figure 29:
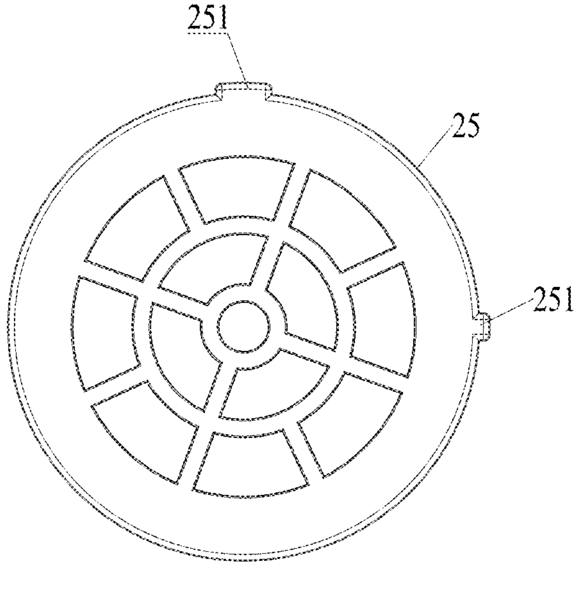
FIG. 29 is a front view of the gas blocking member in FIG. 28.
Figure 30:
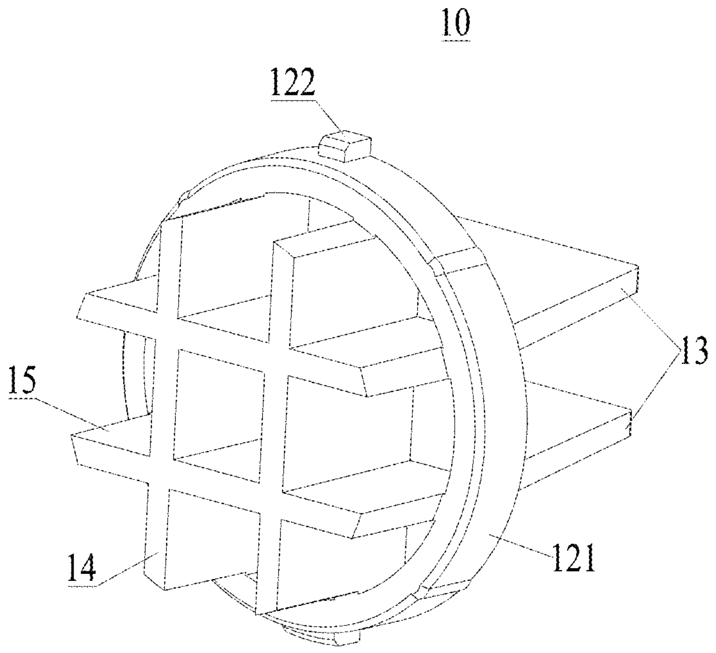
FIG. 30 is a perspective view of another embodiment of the flow guiding member according to the present disclosure.
Figure 31:
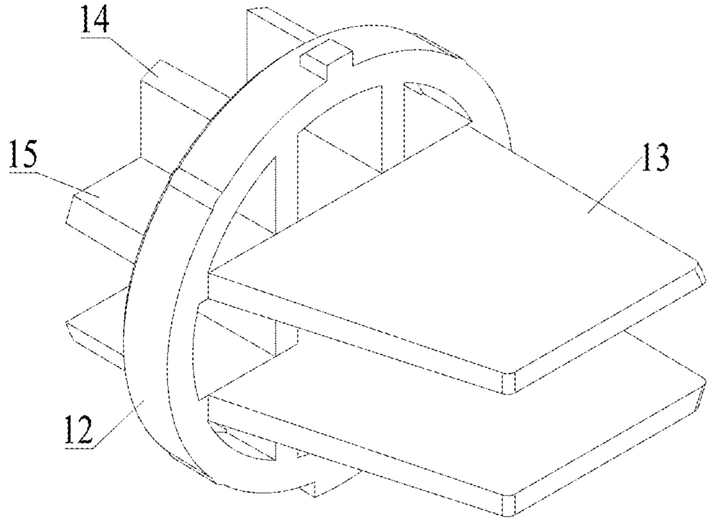
FIG. 31 is a perspective view of another angle of the flow guiding member in FIG. 30.
Figure 32:
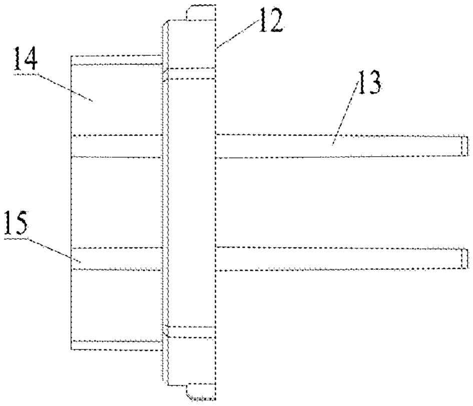
FIG. 32 is a front view of the flow guiding member in FIG. 30.
Figure 33:
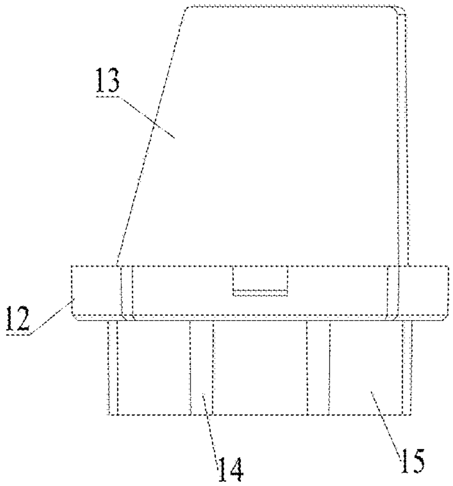
FIG. 33 is a top view of the flow guiding member in FIG. 30.
Figure 34:
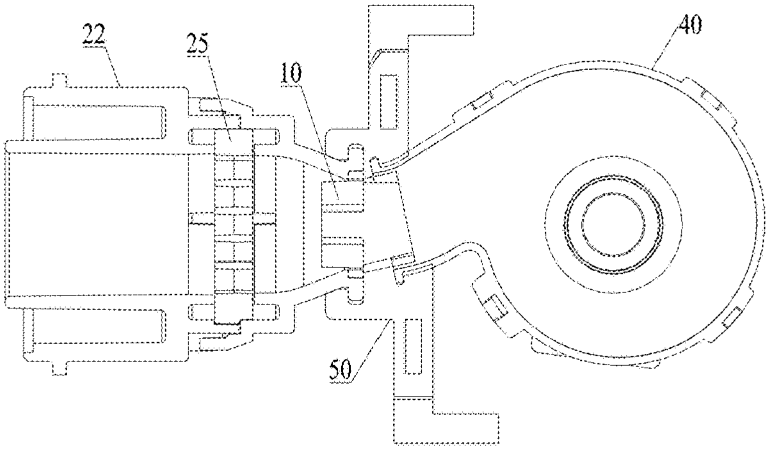
FIG. 34 is a transversely sectional view of the flow guiding member in FIG. 30 installed to the ventilating tube assembly and the fan.

In the above embodiment, it may be understood that the gas blocking member 25 does not completely block the communication between the gas-inlet cavity 212 and the gas-outlet cavity 222, and the gas blocking member 25 is provided with an opening communicating the gas-inlet cavity 212 and the gas-outlet cavity 222 (refer to FIGS. 28 and 29). The gas blocking member 25 plays a role to generate a pressure differential between the gas-inlet cavity 212 and the gas-outlet cavity 222, so as to measure the flow rate of the gas inside the ventilation cavity by using the pressure differential. The flow guiding member 10 may be provided with any suitable shape and structure, as long as it may guide the gas flow from the gas-outlet channel 41 to enter the gas-inlet cavity 212 in the axial direction of the ventilation cavity.

In the ventilating device according to the present disclosure, by using the above technical solution, in usage, referring to FIG. 22, the gas discharged from the gas outlet 42 of the fan 40 enters the flow guiding member 10, is guided by the flow guiding member 10 to stably enter the gas-inlet cavity 212 in the axial direction of the ventilation cavity of the ventilating tube assembly 20, and subsequently stably flows toward the gas-outlet port 221 of the ventilating tube assembly 20 in the axial direction of the ventilation cavity. Moreover, due to the gas blocking member 25 disposed inside the ventilation cavity, the gas-inlet cavity 212 plays a role as a high-pressure cavity, and the gas-outlet cavity 222 plays a role as a low-pressure cavity. By using the first collecting branch tube 23 and the second collecting branch tube 24 to collect the air pressures inside the gas-inlet cavity 212 and the gas-outlet cavity 222, respectively, the pressure differential between the two sides of the gas blocking member 25 may be obtained, and the gas flow rate inside the ventilation cavity is obtained. The function of guiding of the flow guiding member 10 may prevent generation of turbulence, eddy current and so on when the gas is entering the ventilation cavity, which may effectively improve the stability of the gas flow inside the ventilation cavity, to enable the measured pressure-differential value between the two sides of the gas blocking member 25 to be more stable, whereby the final obtained value of the flow rate inside the ventilation cavity is more accurate, thereby effectively improving the reliability of the flow-rate monitoring of the ventilation-treatment device, and ensuring the usage safety of the patient.

Figure 23:
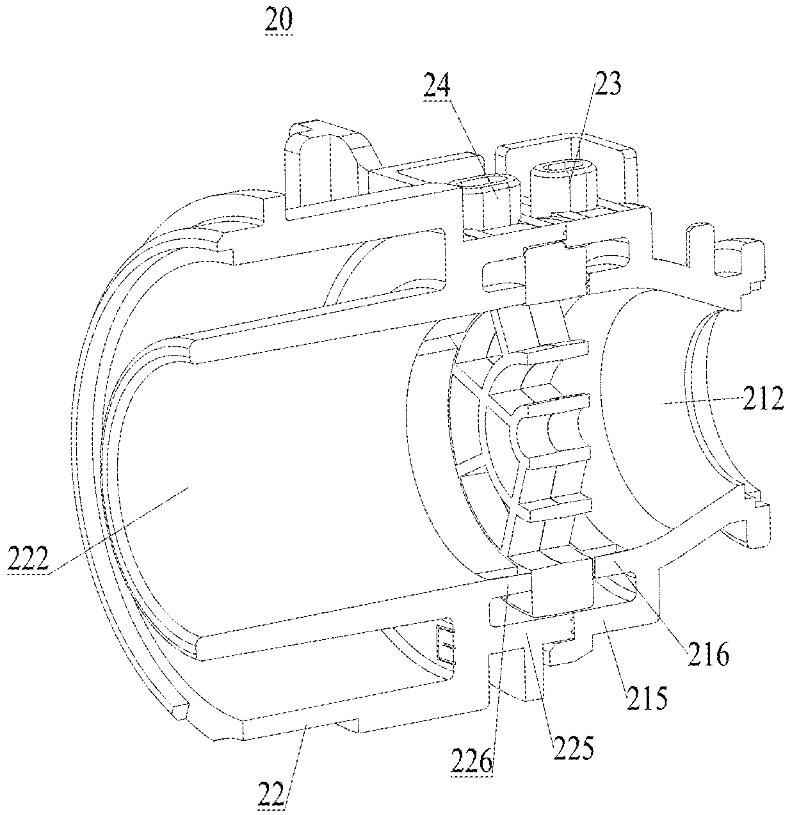
FIG. 23 is a schematic diagram of another angle of the ventilating tube assembly installed with the gas blocking member in FIG. 20.
Figure 24:
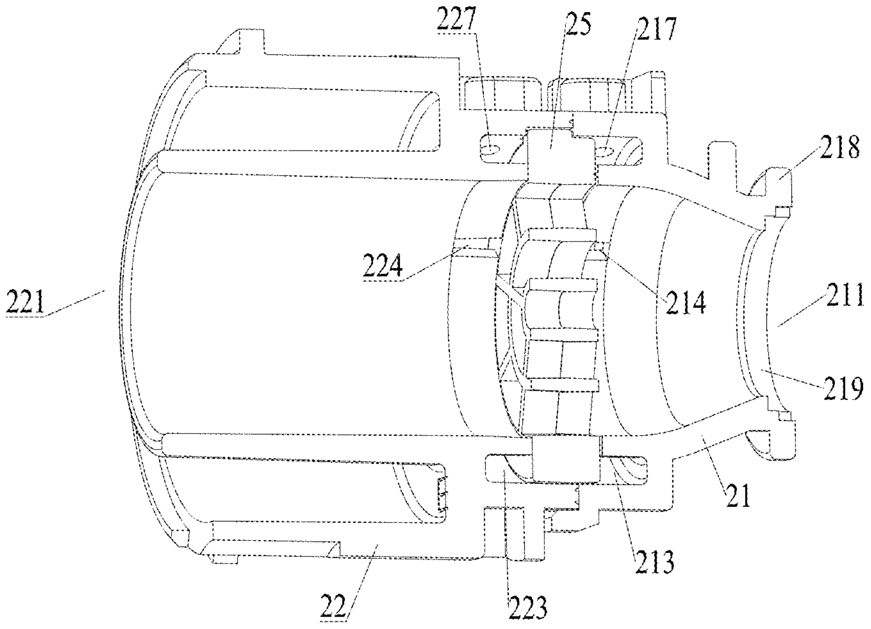
FIG. 24 is a schematic diagram of another angle of FIG. 23.

In order to further improve the stability of the measured pressure differential, referring to FIGS. 23 and 24, the ventilating tube assembly 20 may include a first tube wall for forming the gas-inlet cavity 212 and a second tube wall for forming the gas-outlet cavity 222, the first tube wall is formed with a first gas cavity 213 therein, the first tube wall is provided with a first communicating opening 214 communicating the gas-inlet cavity 212 and the first gas cavity 213, the second tube wall is formed with a second gas cavity 223 therein, and the second tube wall is provided with a second communicating opening 224 communicating the gas-outlet cavity 222 and the second gas cavity 223; and the first collecting branch tube 23 is disposed outside the first tube wall and communicates with the first gas cavity 213, and the second collecting branch tube 24 is disposed outside the second tube wall and communicates with the second gas cavity 223.

By forming the first gas cavity 213 communicate with the gas-inlet cavity 212 in the first tube wall, and the second gas cavity 223 communicate with the gas-outlet cavity 222 forming in the second tube wall, part of the gas flows inside the gas-inlet cavity 212 and the gas-outlet cavity 222 may enter the first gas cavity 213 and the second gas cavity 223, respectively, and the first gas cavity 213 and the second gas cavity 223 may effectively alleviate the affection by the gas-flow fluctuation in the gas-inlet cavity 212 and the gas-outlet cavity 222 on the gas-flow stability inside the first gas cavity 213 and the second gas cavity 223 as pressure stabilizing components. By using the first collecting branch tube 23 and the second collecting branch tube 24 to collect the air pressures in the first gas cavity 213 and the second gas cavity 223 for the pressure-differential measurement, respectively, the measured pressure-differential value between the two sides of the gas blocking member 25 may be more accurate, whereby the final obtained value of the flow rate of the ventilation cavity is more accurate.

In the present disclosure, the ventilating tube assembly 20 may be integrally formed, and may also be formed by connecting multiple components. Moreover, in order to simplify the manufacturing process of the ventilating tube assembly 20 and reduce the manufacturing cost, for example, as shown in FIGS. 18-21, the ventilating tube assembly 20 may include a first tube piece 21 and a second tube piece 22 that are connected, the first tube piece 21 includes the gas-inlet port 211, the gas-inlet cavity 212 and the first tube wall, the second tube piece 22 includes the gas-outlet port 221, the gas-outlet cavity 222 and the second tube wall, and the gas blocking member 25 is between the first tube piece 21 and the second tube piece 22.

The first gas cavity 213 may be located at any position of the first tube wall, and the second gas cavity 223 may be located at any position of the second tube wall. However, in order to further increase the accuracy of the flow-rate measurement, preferably, the first gas cavity 213 and the second gas cavity 223 are disposed adjacent to the gas blocking member 25.

Particularly, according to an embodiment of the present disclosure, the first tube piece 21 is provided with a first port for connecting to the second tube piece 22 (refer to the left port of the first tube piece 21 in FIG. 19). The first tube wall includes a first annular wall 215 for forming the first port and a second annular wall 216 coaxially nested inside the first annular wall 215, a radial gap exists between the first annular wall 215 and the second annular wall 216 is configured to form the gas-inlet cavity 212, and the first communicating opening 214 is disposed in the second annular wall 216 (refer to FIGS. 23 and 24). The second tube piece 22 is provided with a second port for connecting to the first tube piece 21 (refer to the right port of the second tube piece 22 in FIG. 19). The second tube wall includes a third annular wall 225 for forming the second port and a fourth annular wall 226 coaxially nested inside the third annular wall 215, a radial gap exists between the third annular wall 225 and the fourth annular wall 226 is configured to form the gas-outlet cavity 222, and the second communicating opening 224 is disposed in the fourth annular wall 226 (refer to FIGS. 23 and 24). The gas blocking member 25 is between the first port and the second port, and blocks the communication between the gas-inlet cavity 212 and the gas-outlet cavity 222 (refer to FIGS. 23 and 24).

In the above embodiment, referring to FIG. 19, the right end of the first tube piece 21 is formed as the gas-inlet port 211, and the first port plays a role as the gas outlet of the first tube piece 21; and the left end of the second tube piece 22 is formed as the gas-outlet port 221, and the second port plays a role as the gas inlet of the second tube piece 22. The first tube piece 21 and the second tube piece 22 are connected and communicated via the first port and the second port. In addition, it should be noted that the design of the gas blocking member 25 is closely related to the positions of the first communicating opening 214 and the second communicating opening 224, wherein the positions of the first communicating opening 214 and the second communicating opening 224 are required to be correspondingly adjusted according to the different designs of the gas blocking member 25, to avoid to the greatest extent the structural design points where eddy current, turbulence and so on are easily generated.

In the above embodiment, in order to implement the communication between the first collecting branch tube 23 and the first gas cavity 213, a first opening 217 communicate with the first collecting branch tube 23 may be disposed in the first annular wall 215 (refer to FIG. 24). Optionally, in order to enable the air pressure collected by the first collecting branch tube 23 to be more stable, as shown in FIG. 24, preferably, the first opening 217 and the first communicating opening 214 are far from each other in the circumferential direction of the first port. That may reduce the affection on the air-pressure collection by the gas intake of the first gas cavity 213.

Figure 25:
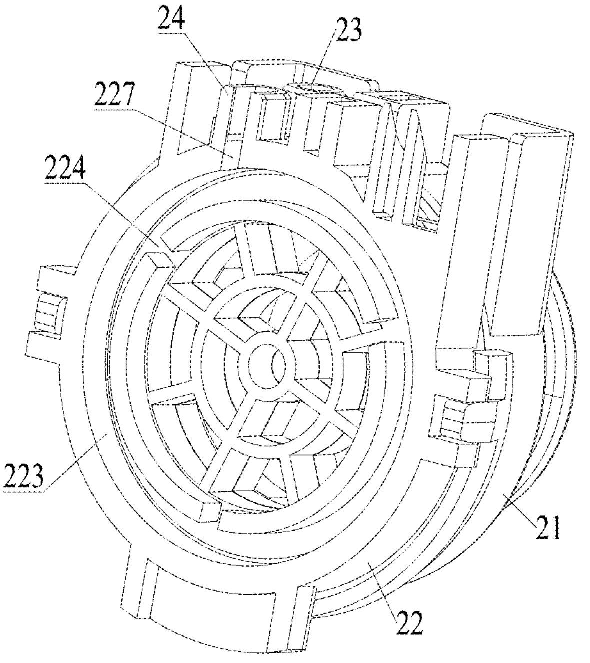
FIG. 25 is a longitudinally sectional view of FIG. 18.

In order to implement the communication between the second collecting branch tube 24 and the second gas cavity 223, a second opening 227 communicate with the second collecting branch tube 24 may be disposed in the third annular wall 225 (refer to FIG. 24). Optionally, in order to enable the air pressure collected by the second collecting branch tube 24 to be more stable, as shown in FIGS. 24 and 25, preferably, the second opening 227 and the second communicating opening 224 are far from each other in the circumferential direction of the second port. That may reduce the affection on the air-pressure collection by the gas intake of the second gas cavity 223.

In the present disclosure, in order to further increase the accuracy of the flow-rate measurement, as shown in FIGS. 24 and 25, preferably, the first opening 217 and the second opening 227 are located in the same axis of the ventilation cavity, and the first communicating opening 214 and the second communicating opening 224 are located in the same axis of the ventilation cavity.

In the present disclosure, in order to improve the effect of pressure stabilization of the first gas cavity 213, at least two first communicating openings 214 may be disposed in the second annular wall 216. Preferably, the first communicating openings 214 are 2-3 first communicating openings. The plurality of first communicating openings 214 are disposed at intervals in the circumferential direction of the second annular wall 216. Similarly, in order to improve the effect of pressure stabilization of the second gas cavity 223, at least two second communicating openings 224 may be disposed in the fourth annular wall 226. Preferably, the second communicating openings 224 are 2-3 second communicating openings. The plurality of second communicating openings 224 are disposed at intervals in the circumferential direction of the fourth annular wall 226 (refer to FIG. 25).

As shown in FIGS. 24 and 25, the first communicating opening 214 may be formed at the end of the second annular wall 216 in a slotted form, and the second communicating opening 224 may be formed at the end of the fourth annular wall 226 in a slotted form. That may further reduce the manufacturing cost of the ventilating device, and avoid the positions inside the gas-inlet cavity 212 and the gas-outlet cavity 222 where eddy current and turbulence are easily generated.

In the present disclosure, in order to ensure the reliability of the connection between the first port and the second port, and the stability of the disposing of the gas blocking member 25 by the first port and the second port, as shown in FIGS. 23 and 24, optionally, the end of the first annular wall 215 is located outside the end of the second annular wall 216 in the axial direction of the first port, the end of the third annular wall 225 is located outside the end of the fourth annular wall 226 in the axial direction of the second port, the end surface of the first annular wall 215 and the end surface of the third annular wall 225 abut, the gas blocking member 25 is disk-like, the peripheral surface of the gas blocking member 25 abuts the inner surface of the first annular wall 215 and/or the third annular wall 225, and the two side surfaces of the gas blocking member 25 abut the end surface of the second annular wall 216 and the end surface of the fourth annular wall 226.

In the above embodiment, the first tube piece 21 and the second tube piece 22 may be further integrated by welding the end surface of the first annular wall 215 and the end surface of the third annular wall 225.

In the present disclosure, in order to improve the convenience and the reliability of the assembling between the first tube piece 21, the second tube piece 22 and the gas blocking member 25, the ventilating device may further include a first positioning component and a second positioning component. The first positioning component may be configured for the positioning between the first tube piece 21 and the second tube piece 22, and limits the relative rotation between the first tube piece 21 and the second tube piece 22. The second positioning component may be configured for the positioning of the gas blocking member 25 in the ventilating tube assembly 20, and limits the rotation of the gas blocking member 25 with respect to the ventilating tube assembly 20.

Figure 18:
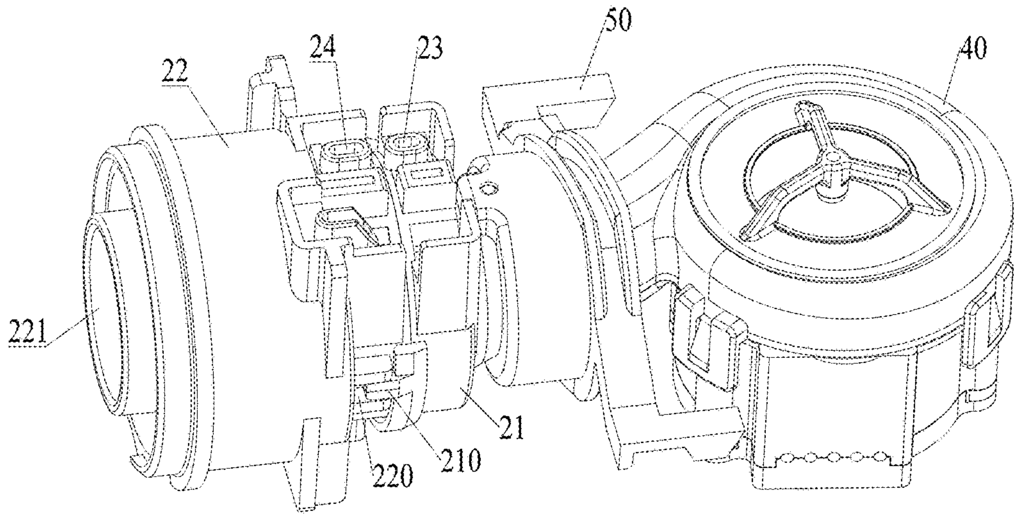
FIG. 18 is a schematic diagram after the flow guiding member, the gas blocking member, the ventilating tube assembly, the fan and the connecting member in FIG. 15 have been assembled.

In an embodiment of the first positioning component according to the present disclosure, the first positioning component may include a first positioning member 210 and a first positioning slot 220 that match to each other, the first positioning member 210 is disposed at one of the first tube piece 21 and the second tube piece 22, and the first positioning slot 220 is disposed at the other of the first tube piece 21 and the second tube piece 22. Particularly, for example, as shown in FIGS. 18 and 19, the first positioning member 210 is disposed on the outer surface of the first annular wall 215 of the first tube piece 21, and the first positioning slot 220 is disposed on the outer surface of the third annular wall 225 of the second tube piece 22. When the first positioning member 210 is inserted into the first positioning slot 220, the positions of the first opening 217 and the second opening 227 correspond, and the positions of the first communicating opening 214 and the second communicating opening 224 correspond. The first positioning member 210 and the first positioning slot 220 may be a plurality of pairs of positioning members and positioning slots.

In an embodiment of the second positioning component according to the present disclosure, the second positioning component may include a second positioning member 251 and a second positioning slot that match, the second positioning member 251 is disposed at one of the gas blocking members 25 and the ventilating tube assembly 20, and the second positioning slot is disposed at the other of the gas blocking member 25 and the ventilating tube assembly 20. Particularly, for example, as shown in FIGS. 23 and 28, the second positioning member 251 is disposed on the peripheral surface of the gas blocking member 25, and the second positioning slot is disposed on the inner surface of the third annular wall 225 of the second tube piece 22. The second positioning member 251 and the second positioning slot may be a plurality of pairs of positioning members and positioning slots.

Figure 26:
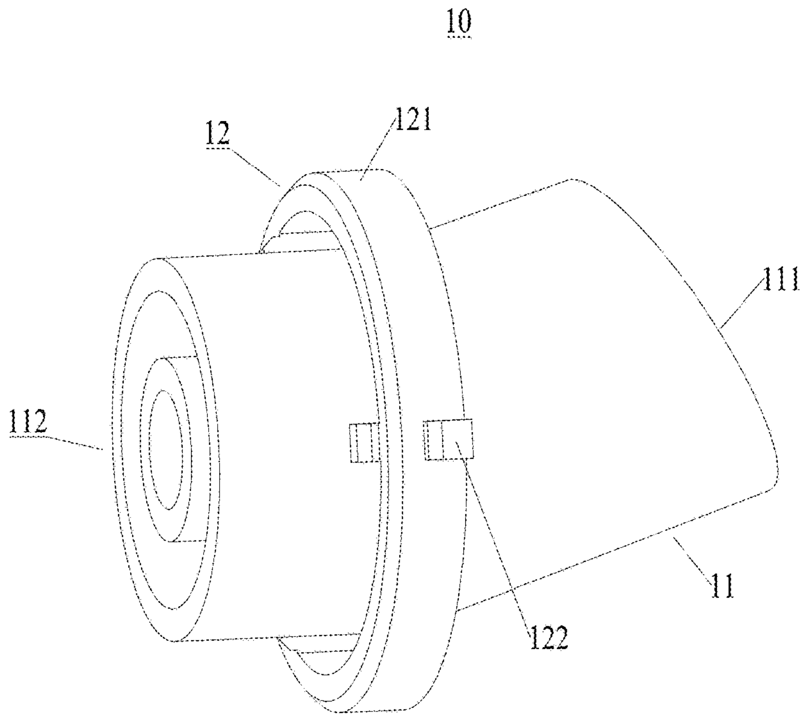
FIG. 26 is a perspective view of the flow guiding member in FIG. 19.
Figure 27:
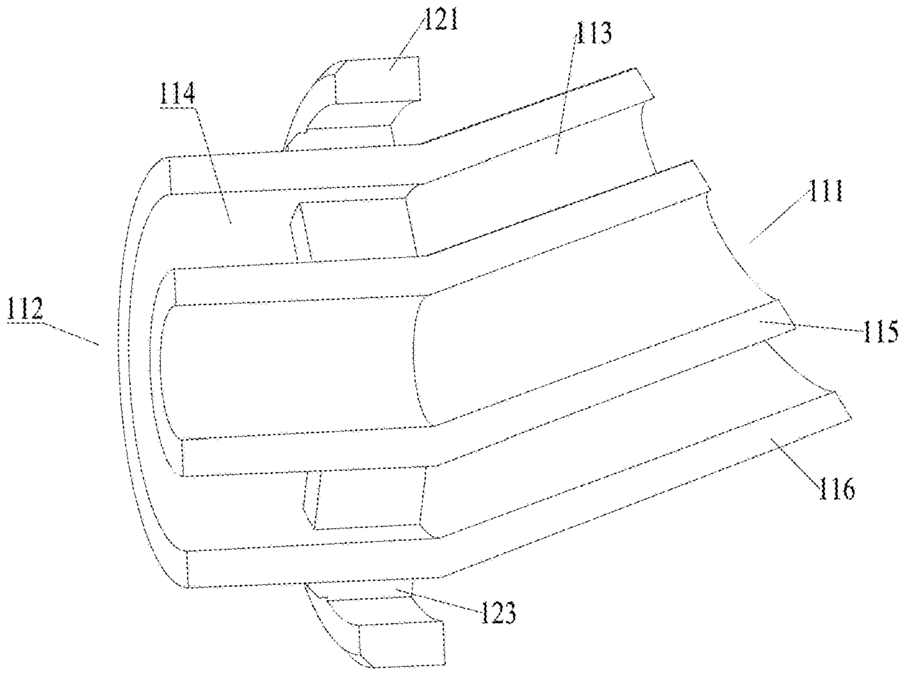
FIG. 27 is a transversely sectional view of the flow guiding member in FIG. 26.

In an embodiment of the flow guiding member 10 according to the present disclosure, referring to FIGS. 20, 26 and 27, the flow guiding member 10 may include a tube body 11 forming a lumen, and a first tube orifice 111 and a second tube orifice 112 that are communicate with the lumen which are opposite to each other, the lumen is divided into a first lumen 113 close to the first tube orifice 111 and a second lumen 114 close to the second tube orifice 112 in the extension direction of the tube body 11, the first tube orifice 111 protrudes into the gas-outlet channel 41, the first lumen 113 is coaxial with the gas-outlet channel 41, the second tube orifice 112 protrudes into the gas-inlet cavity 212, and the second lumen 114 is coaxial with the gas-inlet cavity 212.

In the above embodiment, it should be noted that, as shown in FIGS. 20 and 22, an included angle exists between the axial direction of the ventilation cavity of the ventilating tube assembly 20 and the axial direction of the gas-outlet channel 41 of the fan 40. In this case, an included angle exists between the axial direction of the first lumen 113 and the axial direction of the second lumen 114, wherein the included angle is equal to the included angle between the axial direction of the ventilation cavity and the axial direction of the gas-outlet channel 41. In other words, in practical manufacturing, the included angle between the axial direction of the first lumen 113 and the axial direction of the second lumen 114 may be determined according to the included angle between the axial direction of the ventilation cavity and the axial direction of the gas-outlet channel 41. In addition, both of the part of the tube body 11 that is for forming the first lumen 113 and the part of the tube body 11 that is configured for forming the second lumen 114 are a straight tube (refer to FIG. 26). The tube body 11 may be integrally formed, and may also be formed by connecting the part for forming the first lumen 113 and the part for forming the second lumen 114. The first lumen 113 and the second lumen 114 may be formed in any suitable shape, for example a prism cavity and a cylinder cavity. Preferably, both of the first lumen 113 and the second lumen 114 are a cylinder cavity.

By using the flow guiding member 10, in usage, the gas flowing out of the gas outlet 42 of the fan 40 may enter the first lumen 113 via the first tube orifice 111 of the flow guiding member 10 and flow in the axial direction of the first lumen 113, and then the gas subsequently enter the second lumen 114 and flow inside, and subsequently stably flow into the ventilation cavity from the second tube orifice 112 in the same direction as the axial direction of the ventilation cavity (as shown by the arrow in FIG. 22). Accordingly, the gas flowing out of the gas outlet 42 of the fan 40 does not generate turbulence, eddy current and so on inside the ventilation cavity because the axial directions of the ventilation cavity and the gas-outlet channel 41 are different, to cause instability of the gas flow, which affects the collection and monitoring of the flow rate inside the ventilation cavity.

In the present disclosure, in order to control the gas flow rate flowing through the lumen, as shown in FIGS. 26 and 27, the tube body 11 may include an inner tube body 115 and an outer tube body 116 that are coaxially nested, a first radial gap exists between the inner tube body 115 and the outer tube body 116. When the lumen is a cylinder cavity, the cross-sections of the inner tube body 115 and the outer tube body 116 are circular.

In addition, in order to facilitate the installing of the flow guiding member 10 in the ventilating tube assembly 20 or the fan 40, the flow guiding member 10 may further include a installing base 12, and the installing base 12 is disposed outside the tube body 11 for installing the tube body 11 to the ventilating tube assembly 20 or the fan 40. It should be noted that the installing base 12 may be any component that may install the tube body 11 to the ventilating tube assembly 20 or the fan 40.

According to an embodiment of the present disclosure, as shown in FIGS. 26 and 27, the installing base 12 includes a round ring 121 coaxially nested outside the outer tube body 116. In this case, the round ring 121 may be closely adhered to the outer surface of the outer tube body 116, and a second radial gap exists between the round ring 121 and the outer tube body 116. The round ring 121 may be connected to the outer tube body 116 in any manner; for example, they may be fixedly connected by a connecting rib 123 shown in FIG. 27 located between the round ring 121 and the outer tube body 116.

In the above embodiment, when a second radial gap exists between the round ring 121 and the outer tube body 116, in order to ensure the uniformity of the pressures of the gas flows flowing through the points of the flow guiding member 10, the first radial gap, the second radial gap and the inner diameter of the inner tube body 115 may be configured as: in cross-section of the flow guiding member 10 that passes through the round ring 121, the area of the gap area between the inner tube body 115 and the outer tube body 116, the area of the gap area between the round ring 121 and the outer tube body 116 and the area of the interior area of the inner tube body 115 are equal or approximate. Moreover, as the room for installing of the flow guiding member 10 is limited, the area of the gap area between the inner tube body 115 and the outer tube body 116 and the area of the gap area between the round ring 121 and the outer tube body 116 may be configured to be equal or approximate, and the area of the interior area of the inner tube body 115 may be adjusted properly according to practical situations.

In the present disclosure, when the flow guiding member 10 is installed to the ventilating tube assembly 20 or the fan 40 by using the round ring 121, in order to prevent the round ring 121 from rotating with respect to the ventilating tube assembly 20 or the fan 40, a third positioning member 122 may be disposed on the round ring 121, to position the round ring 121 to the ventilating tube assembly 20 or the fan 40. Particularly, a first installing part 219 for the installing of the flow guiding member 10 may be disposed on the inner surface of the first tube wall. Particularly, the first installing part 219 is configured for the installing with the installing base 12 of the flow guiding member 10, and the structure of the first installing part 219 matches with the structure of the installing base 12, and varies with the structure of the installing base 12. For example, in the embodiment shown in FIG. 20, when the installing base 12 includes the round ring 121, the first installing part 219 may be an annular groove for embedding the round ring 121. Optionally, in order to prevent the round ring 121 from rotating with respect to the first installing part 219, the first installing part 219 may be disposed with a structure which is suitable to the third positioning member 122 disposed on the round ring 121. For example, when the third positioning member 122 is a lug disposed on the outer surface of the round ring 121, the first installing part 219 may be disposed with a third positioning slot for embedding the lug.

In another embodiment of the flow guiding member 10 according to the present disclosure, the flow guiding member 10 includes a first guiding assembly and a second guiding assembly that are connected. The first guiding assembly is configured as it may protrude into the gas-outlet channel 41 of the fan 40, divide the gas flow inside the gas-outlet channel 41 and guide it to flow toward the gas-inlet cavity 212 of the ventilating tube assembly 20. The second guiding assembly is configured as it may protrude into the gas-inlet cavity 212 of the ventilating tube assembly 20, divide the gas flow entering the gas-inlet cavity 212 and guide it to flow in the axial direction of the gas-inlet cavity 212 (refer to FIG. 34).

In the above embodiment, the flow guiding member 10 may further include a installing base 12, and the first guiding assembly and the second guiding assembly may be installed to the installing base 12, and be installed to the ventilating tube assembly 20 or the fan 40 via the installing base 12.

Particularly, the installing base 12 includes the round ring 121 and the third positioning member 122 disposed on the round ring 121 (similar to the structure of the installing base in the flow guiding member shown in FIG. 26). The first guiding assembly includes a first guiding plate 13 extending horizontally from the round ring 121 toward the side in the axial direction of the round ring 121 (refer to the right side in FIG. 32). The first guiding plate 13 may be a plurality of first guiding plates that are mutually disposed at intervals. The second guiding assembly includes a second guiding plate 14 and a third guiding plate 15 extending from the round ring 121 toward the other side in the axial direction of the round ring 121 (refer to the left side in FIG. 32). The second guiding plate 14 and the third guiding plate 15 may intersect with each other, to partition a plurality of gas channels.

For example, as shown in FIGS. 30-33, the first guiding assembly includes two first guiding plates 13 that are parallel to each other and are disposed at intervals, the second guiding assembly includes two second guiding plates 14 that are parallel to each other and are disposed at intervals and two third guiding plates 15 that are parallel to each other and are disposed at intervals, the second guiding plates 14 extend in the vertical direction, the third guiding plates 15 extend in the horizontal direction, the two second guiding plates 14 and the two third guiding plates 15 intersect to form a #shape, and the two first guiding plates 13 are connected to the two third guiding plates 15.

In the present disclosure, in order to facilitate the connection between the fan 40 and the ventilating tube assembly 20, the ventilating device may further include a connector 50, and the gas-inlet port 211 of the ventilating tube assembly 20 is connected to the gas outlet 42 of the fan 40 by the connector 50.

In the present disclosure, the gas-inlet port 211 of the ventilating tube assembly 20 may be connected to the gas outlet 42 of the fan 40 by the connector 50. Particularly, as shown in FIGS. 18-22, the gas-inlet port 211 of the ventilating tube assembly 20 may be inserted into the communicating cavity of the connector 50 via the other opening of the connector 50, and be communicate with the gas outlet 42 of the fan 40 via the communicating cavity.

It should be noted that the axial direction of the gas-inlet port 211 and the axial direction of the ventilation cavity are the same, and the axial direction of the gas outlet 42 and the axial direction of the gas-outlet channel 41 are the same. In this case, the axial directions of the two openings of the connector 50 are different, and the gas-inlet port 211 and the gas outlet 42 are inserted into the communicating cavity of the connector 50 in the different axial directions (refer to FIGS. 20 and 22).

Optionally, in order to ensure the fastness of the installing of the gas-inlet port 211 and the gas outlet 42 inside the communicating cavity, a second installing part 52 for installing the gas-inlet port 211 and a third installing part 53 for installing the gas outlet 42 may be disposed on the housing 51. The second installing part 52 and the third installing part 53 may be formed in any suitable structure. Certainly, the ventilating tube assembly 20 and the fan 40 may be disposed with structures matching with the second installing part 52 and the third installing part 53, respectively. For example, as shown in FIGS. 19 and 22, the ventilating tube assembly 20 may include a first annular flange 218 surrounding the gas-inlet port 211, and the second installing part 52 may be an annular groove for embedding the first annular flange 218. The fan 40 may include a second annular flange 43 surrounding the gas outlet 42, and the third installing part 53 may be an annular groove for embedding the second annular flange 43. By using the connecting structure of the matching flanges and grooves between the ventilating tube assembly 20, the fan 40 and the connector 50, detachable connection between the ventilating tube assembly 20, the fan 40 and the connector 50 may be implemented, which facilitates the assembling and maintenance of the ventilating device. Certainly, the connection between the ventilating tube assembly 20, the fan 40 and the connector 50 is not limited to the employment of the above-described connecting structure.

In the present disclosure, the ventilating device may further include a pressure-differential flow-rate sensor 65, wherein the first collecting branch tube 23 is connected to a high-pressure input point 651 of the pressure-differential flow-rate sensor 65, and the second collecting branch tube 24 is connected to a low-pressure input point 652 of the pressure-differential flow-rate sensor 65. In addition, in order to measure the pressure inside the ventilation cavity, a pressure collecting tube 26 may be installed on the ventilating tube assembly 20, and the pressure collecting tube 26 may communicate with the ventilation cavity and connected to a pressure sensor 63, to monitor the pressure inside the ventilation cavity.

Figure 35:
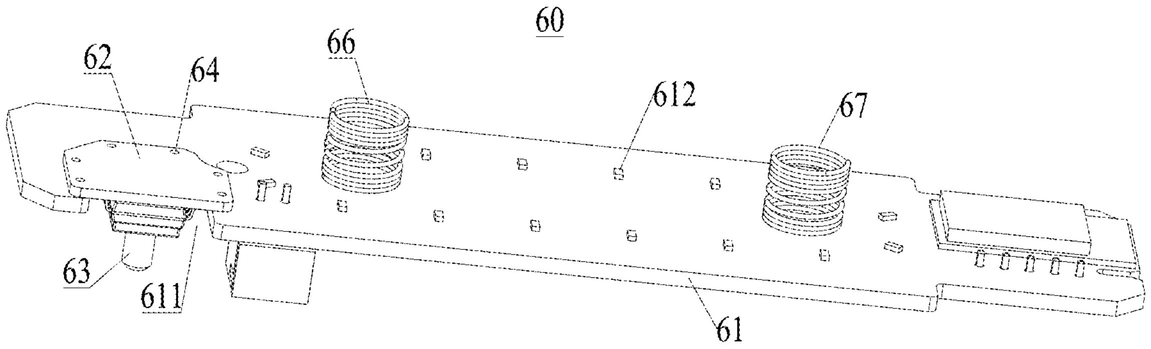
FIG. 35 is a perspective view of the PCBA plate in FIG. 15.
Figure 36:
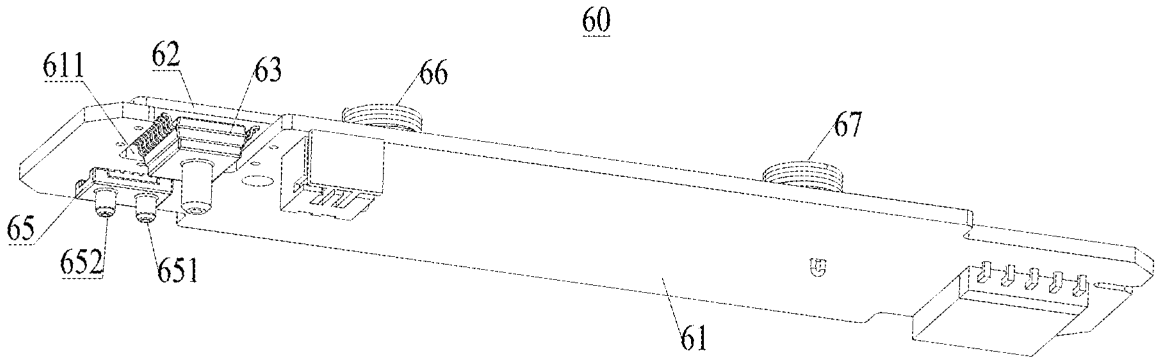
FIG. 36 is a perspective view of another angle of the PCBA plate in FIG. 35.

In order to implement the installation and the usage of the pressure-differential flow-rate sensor 65 and the pressure sensor 63, the ventilating device may further include a PCBA plate 60. The PCBA plate 60 may include a mainboard 61 and a lap-joining board 62. The mainboard 61 is disposed with a through hole 611 that extends throughout the mainboard 61 in the thickness direction of the mainboard 61. The lap-joining board 62 may be lap-joined over or under the through hole 611 according to practical situations of the installation. The pressure-differential flow-rate sensor 65 and the pressure sensor 63 may be installed on the mainboard 61 or the lap-joining board 62 according to practical situations of the installation. When the pressure-differential flow-rate sensor 65 or the pressure sensor 63 is installed on the lap-joining board 62, they should be configured as they may pass through the through hole 611. The position of the through hole 611 on the mainboard 61 may be adjusted according to practical situations of the installation of the sensor installed on the lap-joining board 62. The through hole 611 may be located at the center of the mainboard 61, and may also be located at the edge of the mainboard 61. As shown in FIGS. 35 and 36, when the through hole 611 is located at the edge of the mainboard 61, the through hole 611 is in a slotted form.

The present disclosure, by adding the lap-joining board 62 into the PCBA plate 60, installing the sensor to the lap-joining board 62, and lap-joining the lap-joining board 62 over or under the through hole 611 of the mainboard 61, may implement the regulation of the height of the sensor relative to the mainboard 61, which may prevent interference between the sensor and the component matching with it (for example, the sealing connector 30 described below) when the PCBA plate 60 is installed in the ventilating device, to ensure the reliable connection between the sensor and the matching component.

The lap-joining board 62 may be lap-joined over or under the through hole 611 in any suitable manner. The spacing between the lap-joining board 62 and the mainboard 61 in the thickness direction of the mainboard 61 may be adjusted according to practical demands. For example, in an embodiment, a spacing in the thickness direction of the mainboard 61 exists between the lap-joining board 62 and the mainboard 61, and the lap-joining board 62 and the mainboard 61 are connected by a supporting pillar supporting between the lap-joining board 62 and the mainboard 61. By regulating the height of the supporting pillar, the spacing between the lap-joining board 62 and the mainboard 61 may be regulated, and the electric connection between the lap-joining board 62 and the mainboard 61 is implemented by using the supporting pillar. A plurality of supporting pillars may be disposed between the lap-joining board 62 and the mainboard 61, and the plurality of supporting pillars may be disposed at intervals along the periphery of the through hole 611. In another embodiment, the lap-joining board 62 is directly lap-joined to the mainboard 61; in other words, the spacing between the lap-joining board 62 and the mainboard 61 in the thickness direction of the mainboard 61 is zero (refer to FIGS. 35 and 36), and the lap-joining board 62 and the mainboard 61 are connected by a contact pin 64 penetrating them. It may be understood that both of the lap-joining board 62 and the mainboard 61 are provided with a plughole for the insertion of the contact pin 64. In order to increase the strength of the lap joining, as shown in FIG. 27, the lap-joining board 62 and the mainboard 61 may be connected by a plurality of contact pins 64, and the plurality of contact pins 64 may be disposed at intervals along the periphery of the through hole 611.

Figure 37:
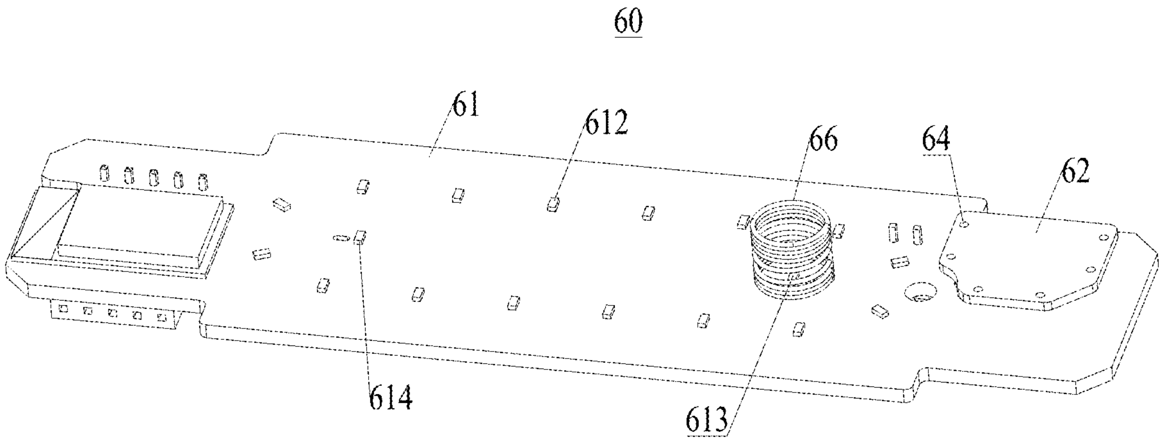
FIG. 37 is a perspective view of yet another angle of the PCBA plate in FIG. 35, wherein the Bluetooth-key touch spring is removed.

In addition, the PCBA plate 60 may further include a spring installed on the mainboard 61. The spring may play a role as a touch spring of a press key in the device, for example, the power-button touch spring 66 and the Bluetooth-key touch spring 67 shown in FIGS. 35 and 36. Furthermore, as shown in FIG. 37, the PCBA plate 60 may further include a device-status light 612, an on-off-status light 613 and a Bluetooth-status light 614 that are installed on the mainboard 61.

In the present disclosure, the ventilating device may further include a sealing connector 30. The first collecting branch tube 23 and the second collecting branch tube 24 may be connected to and communicated with the pressure-differential flow-rate sensor 65 via the sealing connector 30. The pressure collecting tube 26 may be connected to and communicated with the pressure sensor 63 via the sealing connector 30. The sealing connector 30 may be manufactured by using any sealing material, such as silica gel.

In usage, the collecting tubes (i.e., the first collecting branch tube 23, the second collecting branch tube 24 and the pressure collecting tube 26) are used to lead the gas out of the ventilating tube assembly 20, the sensors (i.e., the pressure-differential flow-rate sensor 65 and the pressure sensor 63) are used to collect the corresponding data of the gas, and the sealing connector 30 is configured to deliver the gases led out by the collecting tubes to the sensors, and at the same time prevent gas leakage, which affects the accuracy of the collected data.

Figure 38:
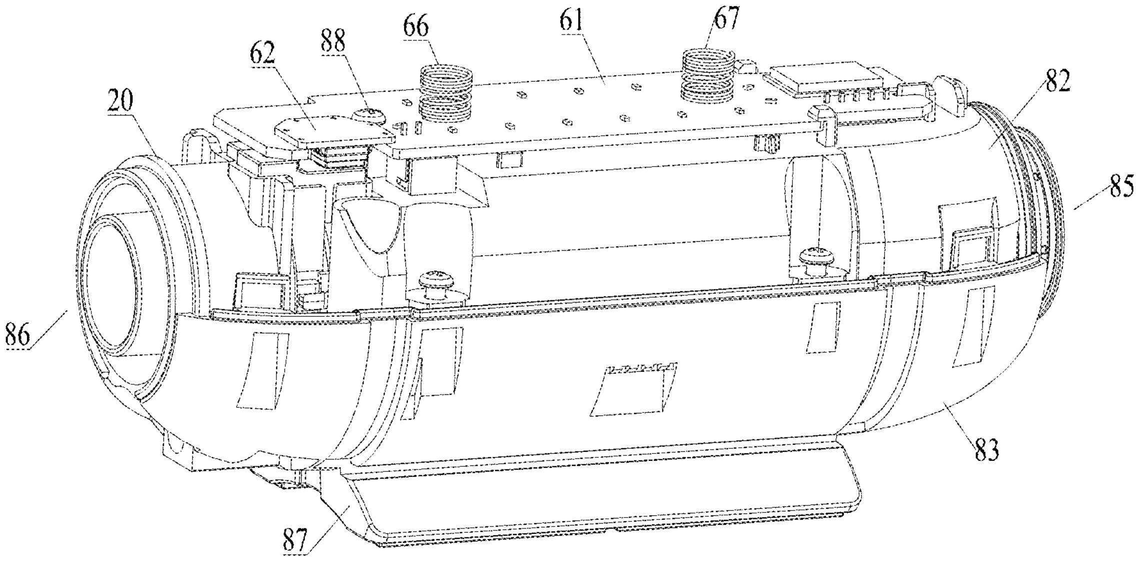
FIG. 38 is a schematic diagram after the decorating assembly and the upper housing have been removed from the ventilating device in FIG. 13.

Particularly, in the embodiments shown in the drawings of the present disclosure, as shown in FIGS. 14 and 38, the first collecting branch tube 23, the second collecting branch tube 24 and the pressure collecting tube 26 are located at the top of the ventilating tube assembly 20, the PCBA plate 60 is installed over the ventilating tube assembly 20, and the sealing connector 30 is located between the ventilating tube assembly 20 and the PCBA plate 60. In the present embodiment, by installing the pressure-differential flow-rate sensor 65 to the mainboard 61, the reliability of the matching and the connection with the sealing connector 30, the first collecting branch tube 23 and the second collecting branch tube 24 may be ensured. However, regarding the pressure sensor 63, if it is installed to the mainboard 61, after the sealing connector 30, the first collecting branch tube 23, the second collecting branch tube 24 and the mainboard 61 are installed in place, the pressure sensor 63 may not be matched with the sealing connector 30 and may interfere the pressure collecting tube 26 or other components because of the distance is too close from the sealing connector 30. Therefore, as shown in FIGS. 35-37, it is required to install the pressure sensor 63 to the lap-joining board 62, and lap-join the lap-joining board 62 over the mainboard 61, which may increase the height of the pressure sensor 63 relative to the mainboard 61, to ensure the reliability of the matching and the connection of the pressure sensor 63 and the sealing connector 30. That prevents interference between the pressure sensor 63 and the other components in the ventilating device while not increasing the occupied space of the PCBA plate 60, thereby increasing the space utilization ratio of the ventilating device, and ensuring a small volume of the ventilating device.

In the present disclosure, the sealing connector 30 may be formed in any suitable structure. According to an embodiment of the present disclosure, referring to FIGS. 40-44, the sealing connector 30 may include a first socket 31 for inserting the pressure sensor 63, a second socket 32 for inserting the pressure collecting tube 26 and a first channel 33 for communicating the first socket 31 and the second socket 32. The first socket 31 and the second socket 32 may be directly or deviatively aligned in the height direction of the sealing connector 30, and the first channel 33 may be straight or curve, which may be particularly adjusted according to practical demands. The sealing connector 30 may further include a third socket 34 for inserting the high-pressure input point 651, a fourth socket 35 for inserting the first collecting branch tube 23 and a second channel for communicating the third socket 34 and the fourth socket 35. The third socket 34 and the fourth socket 35 may be directly or deviatively aligned in the height direction of the sealing connector 30, and the second channel may be straight or curve, which may be particularly adjusted according to practical demands. The sealing connector 30 may further include a fifth socket 36 for inserting the low-pressure input point 652, a sixth socket 37 for inserting the second collecting branch tube 24 and a third channel for communicating the fifth socket 36 and the sixth socket 37. The fifth socket 36 and the sixth socket 37 may be directly or deviatively aligned in the height direction of the sealing connector 30, and the third channel may be straight or curve, which may be particularly adjusted according to practical demands. Certainly, as shown in FIG. 43, when the third socket 34 and the fourth socket 35 are directly aligned in the height direction of the sealing connector 30, the third socket 34 and the fourth socket 35 may be directly communicated, and when the fifth socket 36 and the sixth socket 37 are directly aligned in the height direction of the sealing connector 30, the fifth socket 36 and the sixth socket 37 may be directly communicated.

Figure 43:
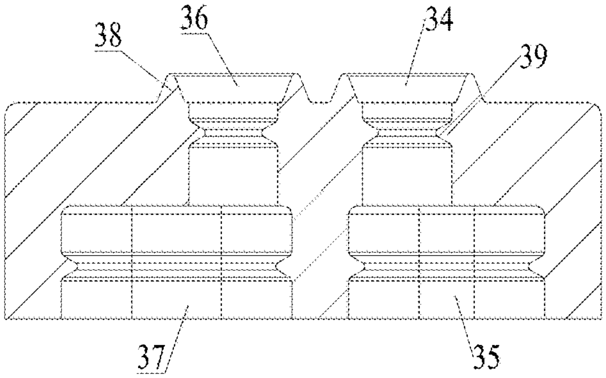
FIG. 43 is a sectional view along the A-A in FIG. 42.
Figure 44:
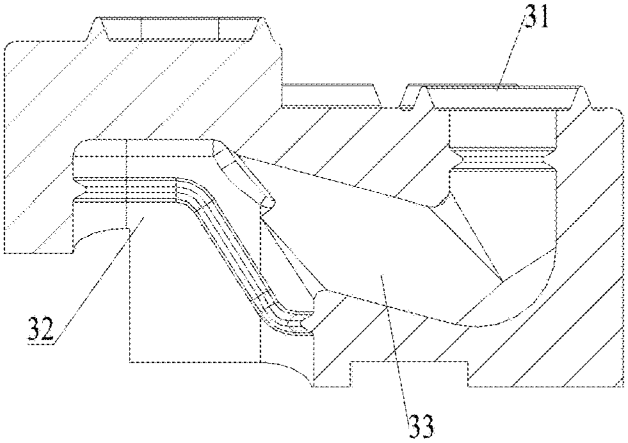
FIG. 44 is a sectional view along the B-B in FIG. 42.

In addition, in order to further improve the sealability of the connection of the sealing connector 30, annular sealing strips may be disposed at the mouth edges and/or the inner walls of the sockets, for example, the first sealing strip 38 and the second sealing strip 39 shown in FIG. 43, wherein the first sealing strip 38 may implement radial sealing, and the second sealing strip 39 may implement axial sealing.

Figure 15:
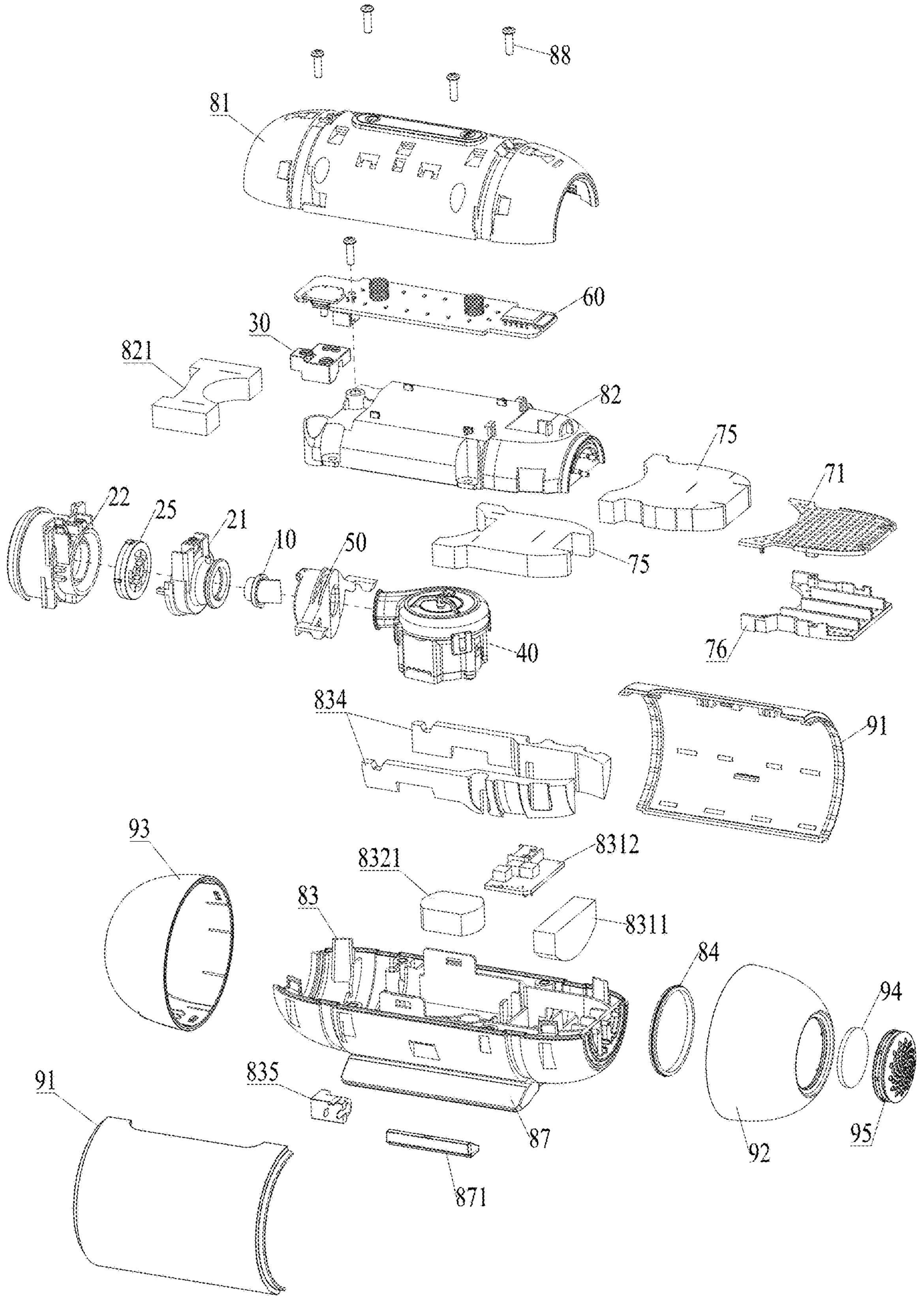
FIG. 15 is an explosive view of the ventilating device in FIG.

In the present disclosure, as shown in FIGS. 14 and 15, the ventilating device may further include a housing assembly 80, the housing assembly 80 includes an internal space, and a gas inlet 85 and a gas outlet 86 that are communicate with the internal space, all of the flow guiding member 10, the ventilating tube assembly 20, the sealing connector 30, the fan 40, the connector 50, the PCBA plate 60 and the noise reducing structure 70 are disposed inside the internal space, the air passage 74 communicates the gas inlet 85 of the housing assembly 80 and the gas inlet 44 of the fan 40, the gas-outlet port 221 of the ventilating tube assembly 20 communicates with the gas outlet 86 of the housing assembly 80, and the other end of the ventilating tube line is connected to the gas outlet 86 of the housing assembly 80.

The housing assembly 80 may be integrally formed, and may also be formed by assembling multiple components. Particularly, in order to reduce the manufacturing cost, increase the assembling efficiency and facilitate the maintenance, according to an embodiment of the present disclosure, as shown in FIGS. 14 and 15, the housing assembly 80 includes an upper housing 81, a middle housing 82 and a lower housing 83, the middle housing 82 covers the top of the lower housing 83, the upper housing 81 covers the top of the middle housing 82, the flow guiding member 10, the ventilating tube assembly 20, the fan 40, the connector 50 and the noise reducing structure 70 are provided inside the cavity formed by the middle housing 82 and the lower housing 83, the gas inlet 85 and the gas outlet 86 are communicate with the cavity formed by the middle housing 82 and the lower housing 83, and the sealing connector 30 and the PCBA plate 60 are provided inside the cavity formed by the middle housing 82 and the upper housing 81.

The upper housing 81, the middle housing 82 and the lower housing 83 may be formed in any suitable shape and structure. Particularly, for example, in the lower housing 83 shown in FIGS. 49 and 50, the right end of the lower housing 83 is the gas inlet 85, the left end of the lower housing 83 is the gas outlet 86, the lower housing 83 forms a gas-inlet chamber 831, a fan chamber 832 and a gas-outlet chamber 833 that are communicate with the gas inlet 85 and the gas outlet 86, and the gas-inlet chamber 831, the fan chamber 832 and the gas-outlet chamber 833 are disposed sequentially in the direction from right to left. Referring to FIG. 14, a gas-inlet noise reducing cotton 8311, an electric assembly 8312 and a sound absorbing cotton 75 in the noise reducing structure 70 that matches with the second micropore plate 76 (i.e., the side sound absorbing cotton described above, wherein its matching with the fan 40 refers to FIG. 60) are disposed inside the gas-inlet chamber 831, and the bottom wall of the lower housing 83 that is configured for forming the gas-inlet chamber 831 plays a role as the second back plate of the noise reducing structure 70. A fan supporting cotton 8321 (i.e., the bottom sound absorbing cotton described above; refer to FIG. 61) is provided inside the fan chamber 832, the fan 40 may be disposed on the fan supporting cotton 8321, and the fan supporting cotton 8321 may function to cushion and damp. The bottom wall of the lower housing 83 that is for forming the fan chamber 832 serves as the bottom wall of the fan installation structure, the fan chamber 832 and the gas-outlet chamber 833 are separated by the first side wall 8322 extending upwardly from the bottom wall of the lower housing 83, the gas-outlet tube 46 of the fan 40 is installed to the installing opening 8323 in the first side wall 8322 by using the connector 50, and the ventilating tube assembly 20 is provided inside the gas-outlet chamber 833.

In addition, in order to improve the sealability after the lower housing 83 and the middle housing 82 are assembled, the ventilating device may further include a sealer 834. As shown in FIG. 49, the lower housing 83 may be disposed with a sealer installing slot 836, and the sealer 834 may be installed inside the sealer installing slot 836. In the assembling with the middle housing 82, the flange 820 on the middle housing 82 (refer to FIG. 48) may closely contact the sealer 834 to implement the sealing (refer to FIGS. 51 and 52), especially for sealing the gas-inlet chamber 831 and part of the fan chamber 832 (refer to the position of the sealer installing slot 836 in FIG. 49).

Figure 50:
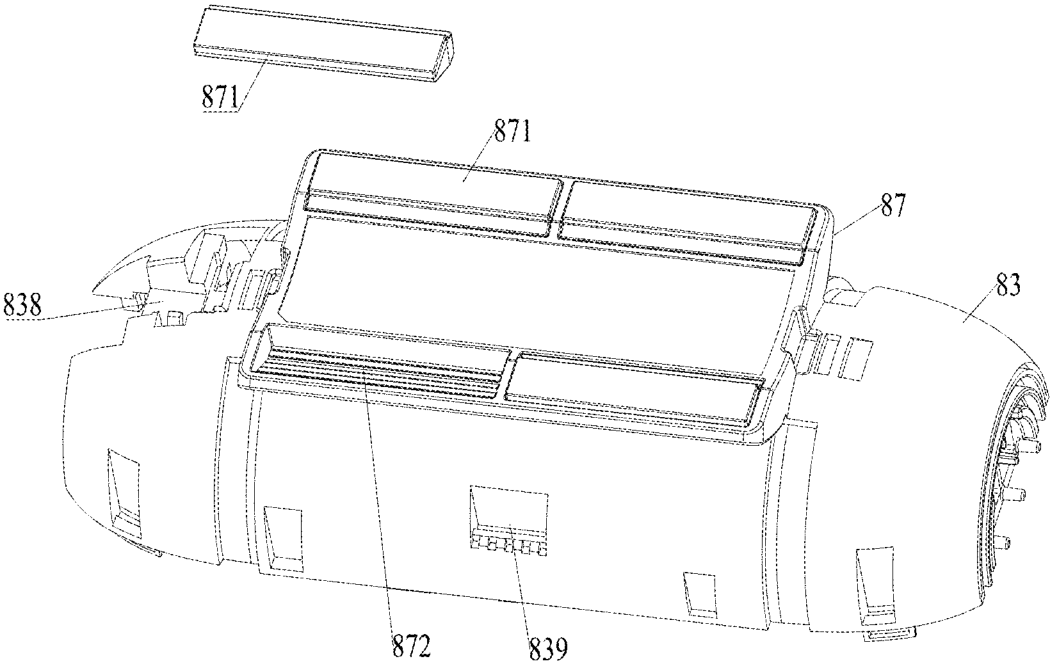
FIG. 50 is a perspective view of another angle of the lower housing in FIG. 49, wherein a slide-proof pad is not installed to the base.

Furthermore, in order to implement electric power supply, the ventilating device may further include a power-supply-socket assembly 835 (refer to FIG. 15), and the power-supply-socket assembly 835 may be installed to the lower housing 83. As shown in FIG. 50, a power-supply-socket installing slot 838 may be disposed on the lower housing 83, and the power-supply-socket assembly 835, after being installed into the power-supply-socket installing slot 838, may be electrically connected to the PCBA plate 60 by using a cable.

As shown in FIG. 50, in order to facilitate the placement of the ventilating device, and improve the stability of the placement of the ventilating device, a base 87 may be disposed at bottom of the lower housing 83. Optionally, in order to prevent the ventilating device from moving in usage, and increase the friction between the base 87 and the placement platform, a slide-proof-gasket installing slot 872 may be disposed at the bottom of the base 87, for installing a slide-proof pad 871. The slide-proof pad 871 may be further fixed inside the slide-proof-gasket installing slot 872 by adhesive bonding.

Figure 47:
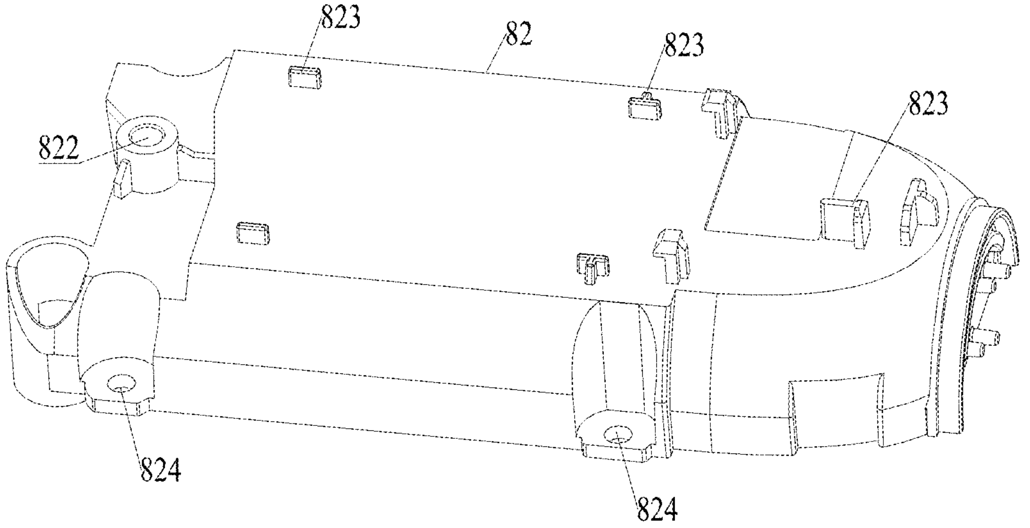
FIG. 47 is a perspective view of the middle housing in FIG. 15.

For example, in the middle housing 82 shown in FIGS. 47 and 48, the right end of the middle housing 82 is the gas inlet 85, the left end of the middle housing 82 is the gas outlet 86, the middle housing 82 forms a sound-absorbing-cotton installing area 825, a fan installing area 826 and a middle-housing noise-reducing-cotton installing area 827, and the sound-absorbing-cotton installing area 825, the fan installing area 826 and the middle-housing noise-reducing-cotton installing area 827 are disposed sequentially from right to left. The sound absorbing cotton 75 in the noise reducing structure 70 that matches with the first micropore plate 71 may be disposed inside the sound-absorbing-cotton installing area 825. In order to prevent the sound absorbing cotton 75 from moving, a sound-absorbing-cotton inserting part 8251 for inserting the sound absorbing cotton 75 is provided inside the sound-absorbing-cotton installing area 825 (refer to FIG. 15, wherein the sound absorbing cotton 75 is provided with a corresponding plughole). A middle-housing noise reducing cotton 821 is provided inside the middle-housing noise-reducing-cotton installing area 827. In order to prevent the middle-housing noise reducing cotton 821 from moving, a middle-housing-noise-reducing-cotton inserting part 8271 for inserting the middle-housing noise reducing cotton 821 is disposed inside the middle-housing noise-reducing-cotton installing area 827 (refer to FIG. 15, wherein the middle-housing noise reducing cotton 821 is provided with a corresponding plughole). A plurality of middle-housing limiting parts 828 are provided inside the middle housing 82, to limit the middle-housing noise reducing cotton 821 and the sound absorbing cotton 75. It should be noted that the top wall of the middle housing 82 that is configured for forming the fan installing area 826 plays a role as the top wall of the fan installation structure, the middle-housing noise reducing cotton 821 and the sound absorbing cotton 75 are the top sound absorbing cotton described above, and the right end walls of the middle housing 82 and the lower housing 83 are the second side wall described above.

Figure 16:
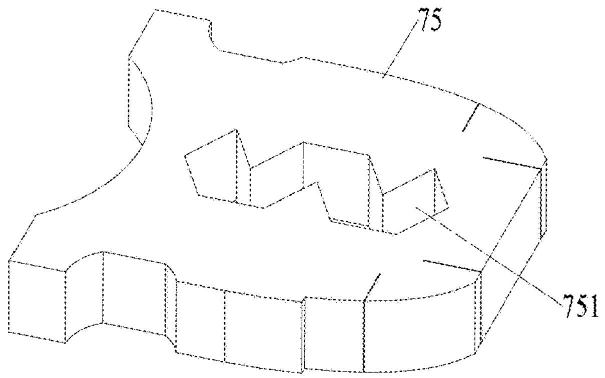
FIG. 16 is a schematic structural diagram of another embodiment of the sound absorbing cotton located above the first micropore plate in FIG. 15.

Referring to FIG. 16, the sound absorbing cotton 75 in the noise reducing structure 70 that matches with the first micropore plate 71 may be provided with a sound-absorbing-cotton through hole 751 in its center, and the area of the inner wall of the sound-absorbing-cotton through hole 751 is greater than its cross-sectional area. By using such a configuration, in an aspect, the sound absorbing area of the sound absorbing cotton may be increased, which improves the effect of noise reduction. In another aspect, the sound-absorbing-cotton through hole 751 may cooperate with the first micropore plate 71 to form a 'narrow-mouthed-bottle-type' cavity (which is similar to a small resonant cavity connected to the side of the air passage), which may reflect back, at the suddenly changing points, the acoustic waves of some frequencies propagated in the air passage, or trap the acoustic waves inside the sound-absorbing-cotton through hole 751 to be reflected repeatedly, thereby achieving the goal of noise elimination. Preferably, as shown in FIG. 16, the sound-absorbing-cotton through hole 751 is a sawtooth-shaped through hole, which may increase the turning points, to further improve the effect of noise reduction by blocking-type noise reduction.

Figure 17:
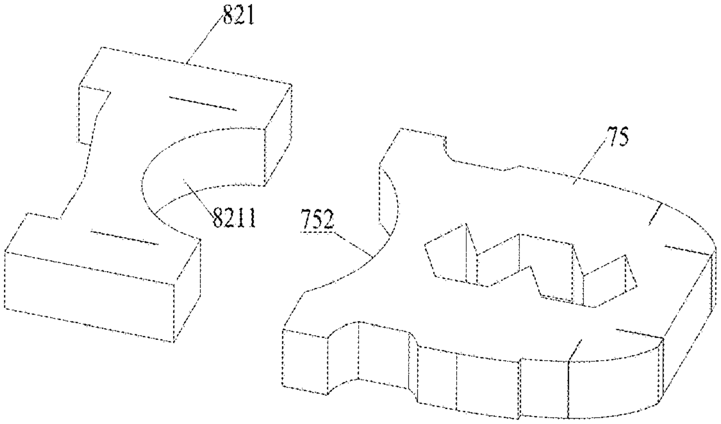
FIG. 17 is a schematic diagram after the sound absorbing cotton in FIG. 16 and the middle-housing noise reducing cotton in FIG. 15 have been assembled to the ventilating device.

Referring to FIG. 17, FIG. 17 shows the position relation after the sound absorbing cotton 75 and the middle-housing noise reducing cotton 821 in FIG. 16 are assembled to the middle housing 82. As shown in the figure, a middle-housing-noise-reducing-cotton arc wall 8211 is formed on the right side of the middle-housing noise reducing cotton 821, a sound-absorbing-cotton arc wall 752 is formed on the left side of the sound absorbing cotton 75, the middle-housing-noise-reducing-cotton arc wall 8211 and the sound-absorbing-cotton arc wall 752 together form a substantially circular chamber, and the chamber is located above the gas inlet 44 of the fan 40. The gas leaving the air passage 74 firstly enters the chamber, and subsequently enters the fan 40 from the chamber via the gas inlet 44. The chamber may cushion the gas from the air passage 74 and ensure the gas input of the fan 40. In addition, the middle-housing-noise-reducing-cotton arc wall 8211 and the sound-absorbing-cotton arc wall 752 form a round-ring-type sound absorbing barrier at the gas inlet 44 of the fan 40, which may not only effectively reduce the noise generated by the gas-flow impact on the air passage, but also may immediately absorb the outwardly diffusing noise generated when the fan 40 is operating.

Referring to FIG. 14, the top wall of the middle housing 82 that is configured for forming the sound-absorbing-cotton installing area 825 may play a role as the first back plate 72 of the noise reducing structure 70. The noise reducing structure 70 shown in FIG. 9 may be installed to the middle housing 82. As shown in FIGS. 9 and 48, a snap-fitting slot 764 may be disposed on the second micropore plate 76, a middle-housing buckle 829 may be disposed on the middle housing 82, and the middle-housing buckle 829 may be snap-fitted to the snap-fitting slot 764.

Figure 51:
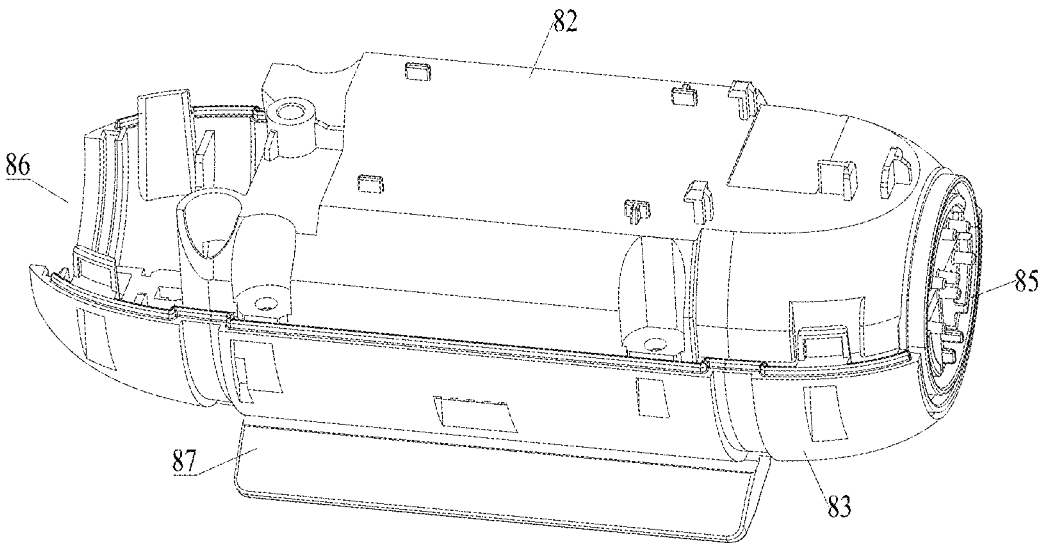
FIG. 51 is a schematic diagram of the middle housing in FIG. 47 installed to the lower housing in FIG. 41.
Figure 52:
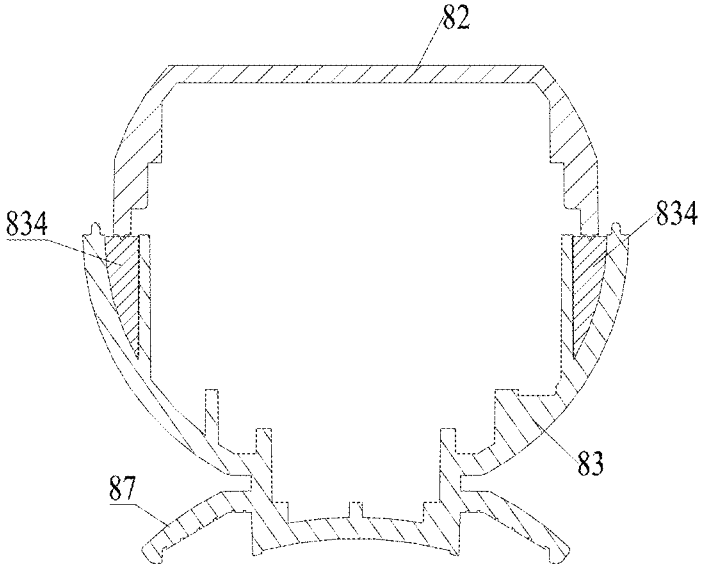
FIG. 52 is a longitudinally sectional view of FIG. 51.

As shown in FIGS. 14 and 51, the sound-absorbing-cotton installing area 825 of the middle housing 82 and the gas-inlet chamber 831 of the lower housing 83 correspond, the fan installing area 826 and the middle-housing noise-reducing-cotton installing area 827 of the middle housing 82 and the fan chamber 832 of the lower housing 83 correspond (the fan installing area 826 and the fan chamber 832 together form the fan installing cavity of the above-described fan installation structure), and in order to facilitate the matching of the ventilating tube assembly 20 with the sealing connector 30 and the PCBA plate 60, the middle housing 82 does not cover the gas-outlet chamber 833 of the lower housing 83.

Figure 39:
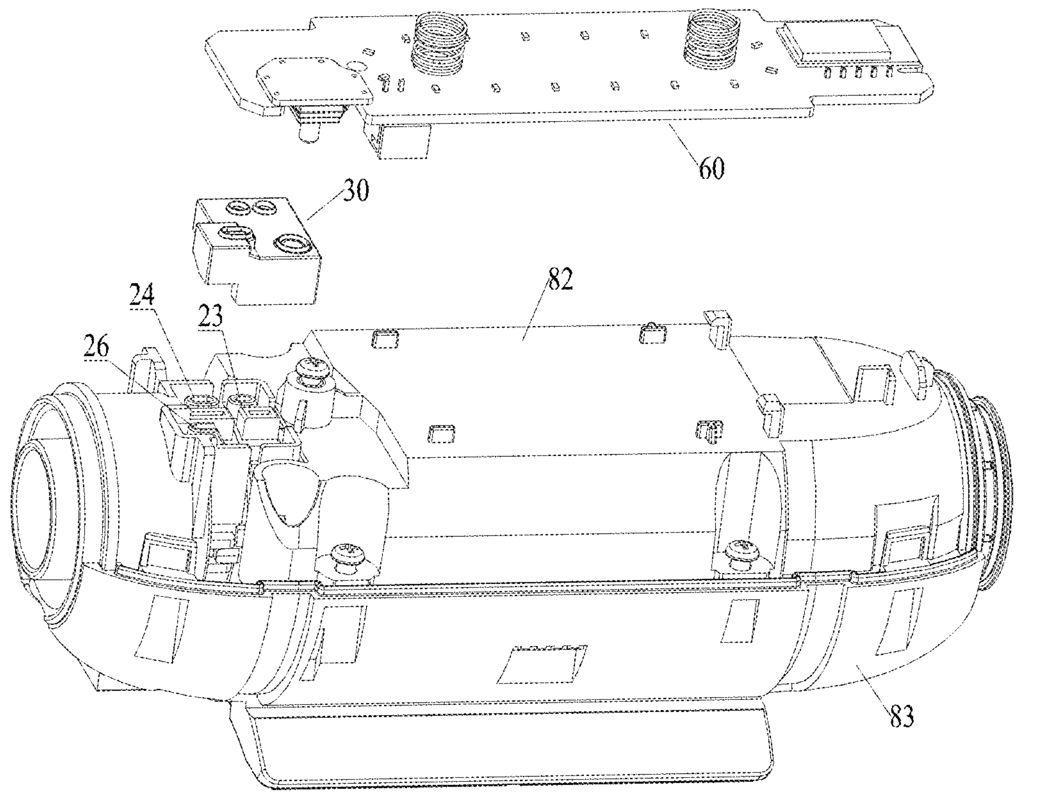
FIG. 39 is an explosive view of FIG. 38.
Figure 40:
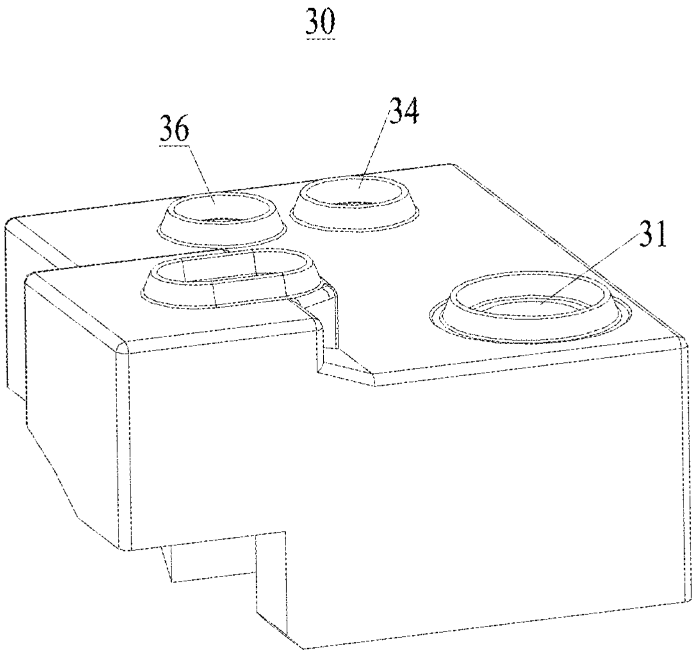
FIG. 40 is a perspective view of the sealing connector in FIG. 39.
Figure 41:
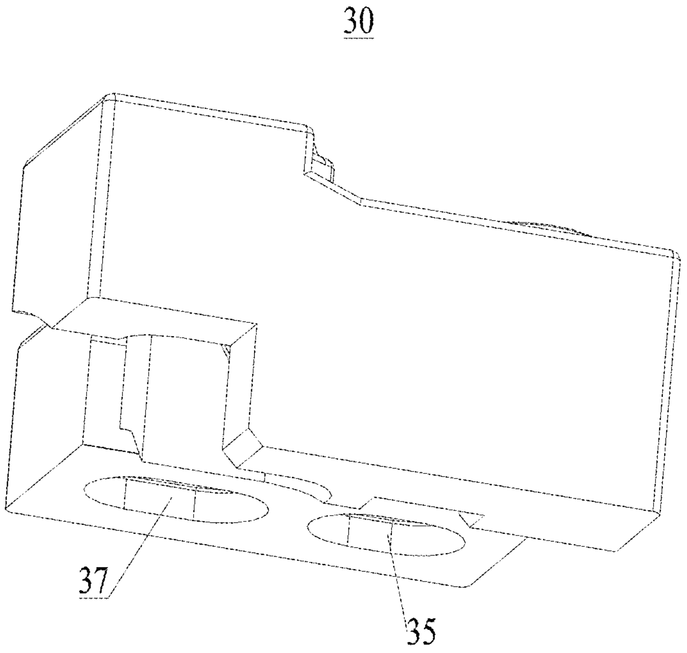
FIG. 41 is a perspective view of another angle of the sealing connector in FIG. 40.
Figure 42:
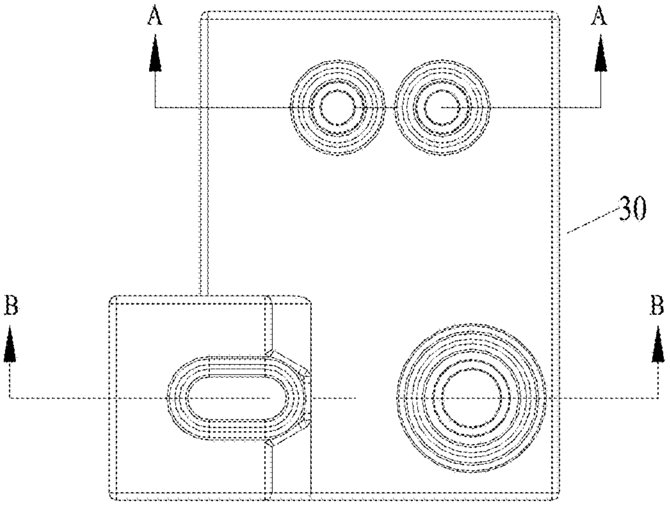
FIG. 42 is a top view of the sealing connector in FIG. 40.

As shown in FIGS. 38, 39 and 47, the PCBA plate 60 is installed above the middle housing 82, and a middle-housing supporting part 823 for supporting the PCBA plate 60 is disposed at the top surface of the middle housing 82. In order to improve the reliability and the fastness of the installing of the PCBA plate 60, the PCBA plate 60 may be fixed to the middle housing 82 by a bolt 88, and the middle housing 82 is disposed with a middle-housing connecting hole 822 for inserting the bolt 88. Certainly, as shown in FIGS. 37 and 38, the mainboard 61 of the PCBA plate 60 is also correspondingly disposed with a hole for inserting the bolt 88.

Figure 45:
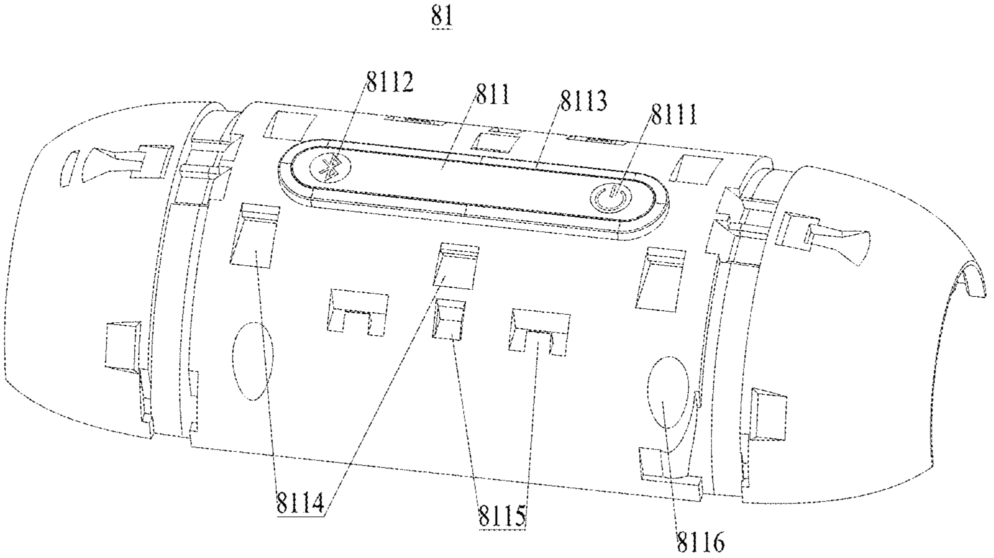
FIG. 45 is a perspective view of the upper housing in FIG. 15.
Figure 46:
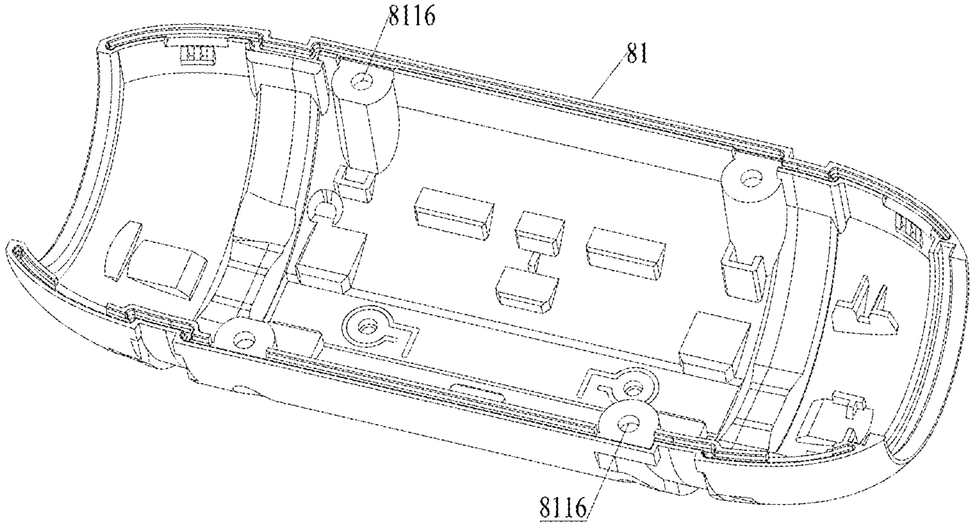
FIG. 46 is a perspective view of another angle of the upper housing in FIG. 45.

For example, in the upper housing 81 shown in FIGS. 45 and 46, the upper housing 81 may be disposed with an operation panel 811, and a power button 8111 and a Bluetooth key 8112 may be disposed in the operation panel 811. Referring to FIG. 14, the power button 8111 and the Bluetooth key 8112 may work with the power-button touch spring 66 and the Bluetooth-key touch spring 67 of the PCBA plate 60, respectively. As shown in FIG. 37, the PCBA plate 60 may further include an on-off-status light 613, a Bluetooth-status light 614 and a device-status light 612 that are disposed on the mainboard 61. In this case, the identifiers on the power button 8111 and the Bluetooth key 8112 may be configured as light-transparent, to facilitate the observation on the on-off-status light 613 and the Bluetooth-status light 614. In addition, a light transmitting ring 8113 may be disposed on the operation panel 811, to facilitate the observation on the device-status light 612, and a plurality of device-status lights 612 are disposed at intervals in the circumferential direction of the light transmitting ring 8113. In the manufacturing of the operation panel 811, the process may include forming by double-shot molding, spraying paint to the surface, subsequently laser-etching the power identifier and the Bluetooth identifier, and finally coating a photosensitizing coating onto the surface. It should be noted that, except the light transmitting area on the operation panel 811, the other positions of the upper housing 81 are preferably lighttight.

Figure 13:
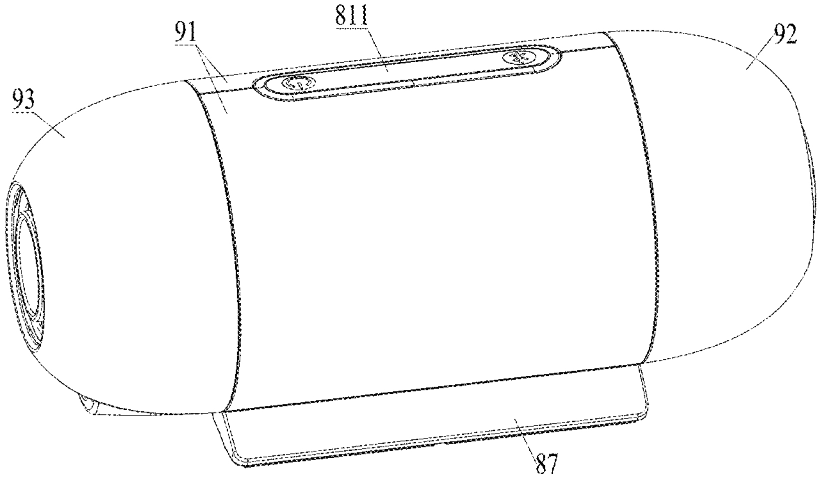
FIG. 13 is a perspective view of an embodiment of the ventilating device according to the present disclosure.

In order to improve the aesthetics of the ventilating device, protect the internal structure of the ventilating device, and reduce the leakage of the noise, the ventilating device may further include a decorating assembly 90, as shown in FIG. 13, the decorating assembly 90 encircles the housing assembly 80, and it is provided with a gas inlet and a gas outlet that correspond to the gas inlet 85 and the gas outlet 86 of the housing assembly 80.

Figure 53:
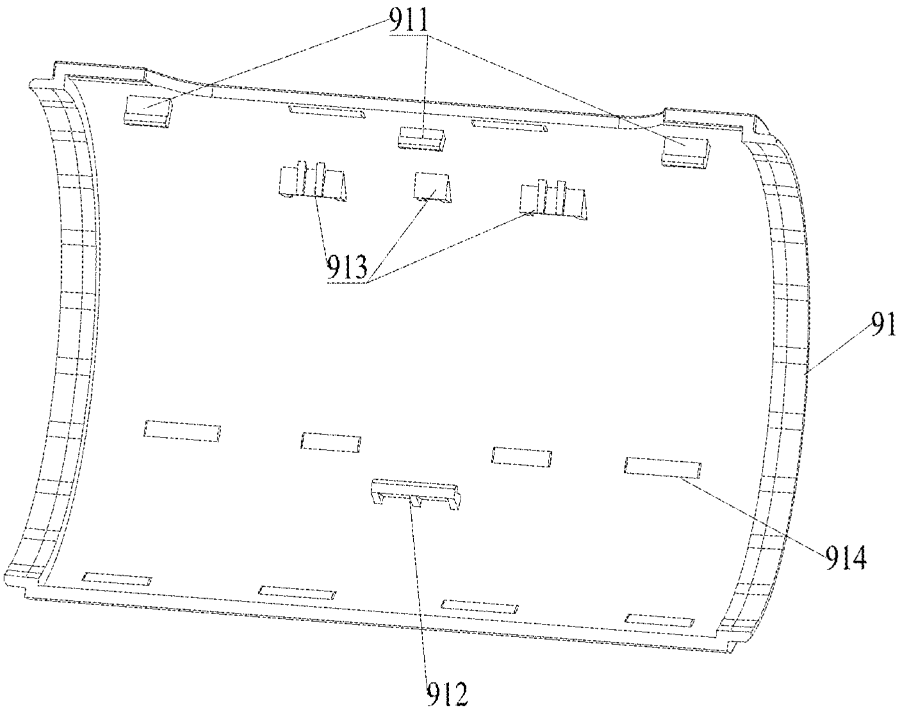
FIG. 53 is a perspective view of the side decorating member in FIG. 15.

As shown in FIGS. 13-15, the decorating assembly 90 may include a gas-inlet decorating member 92, a gas-outlet decorating member 93 and two side decorating members 91. Each of the decorating members is preferably detachably installed outside the housing assembly 80. The two side decorating members 91 may be installed to the two sides of the upper housing 81 and the lower housing 83 by using a buckle structure, and the gas-inlet decorating member 92 and the gas-outlet decorating member 93 may be installed to the gas inlet 85 and the gas outlet 86 by using a buckle structure, respectively. Particularly, for example, as shown in FIGS. 45, 50 and 53, an upper-housing clipping slot 8114 is disposed on the outer wall surface of the upper housing 81, an lower-housing clipping slot 839 is disposed on the outer wall surface of the lower housing 83, and a first buckle 911 matching with the upper-housing clipping slot 8114 and a second buckle 912 matching with the lower-housing clipping slot 839 are provided on the inner wall surface of the side decorating members 91. Certainly, the present disclosure is not limited thereto, wherein the positions of the buckles and the clipping slots may be exchanged, and any other type of the buckle structure may be used.

In order to improve the effect of the assembling between the two side decorating members 91 and the housing assembly 80, and improve the goodness of fit of the assembling between them, as shown in FIGS. 45 and 53, an upper-housing positioning slot 8115 may be provided on the outer wall surface of the upper housing 81, and a positioning part 913 matching with the upper-housing positioning slot 8115 may be disposed on the inner wall surface of the side decorating members 91. The matching between the positioning part 913 and the upper-housing positioning slot 8115 may not only reduce the assembling clearance between the middle part of the side decorating members 91 and the housing assembly 80, but also may improve the reliability of the assembling between them. In addition, a supporting part 914 may be disposed on the inner wall surface of the side decorating members 91, to support the outer wall surfaces of the upper housing 81 and the lower housing 83 after the installing has been in place.

In addition, in order to improve the sealability of the assembling between the gas-inlet decorating member 92 and the housing assembly 80, to prevent gas leakage when the gas is entering the housing assembly 80 from the gas-inlet decorating member 92, as shown in FIG. 15, the ventilating device may further include a sealing ring 84 between the gas inlet 85 of the housing assembly 80 and the gas inlet of the gas-inlet decorating member 92.

In the present disclosure, in order to improve the safety of the ventilation treatment, and reduce the pollution of the entering gas on the internal structure of the ventilating device, as shown in FIGS. 14 and 15, a filtering member may be disposed at the gas inlet of the gas-inlet decorating member 92, to filter the gas entering the housing assembly 80. The filtering member may include a filtering cotton 94 and a filtering-cotton cover 95 for installing the filtering cotton 94. Particularly, the filtering-cotton cover 95 may be installed at the gas inlet of the gas-inlet decorating member 92, the filtering cotton 94 may be installed inside the filtering-cotton cover 95, and the filtering-cotton cover 95 may be disposed with a through hole 951 for the gas to enter.

Figure 54:
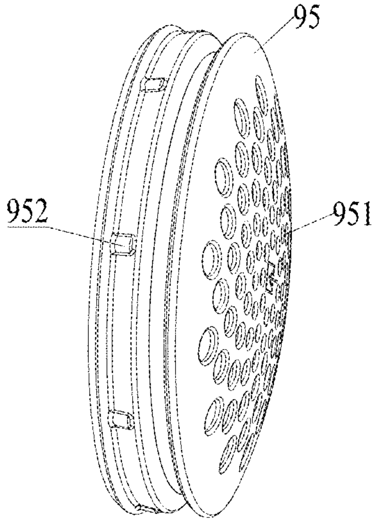
FIG. 54 is a perspective view of the filtering-cotton cover in FIG. 15.
Figure 55:
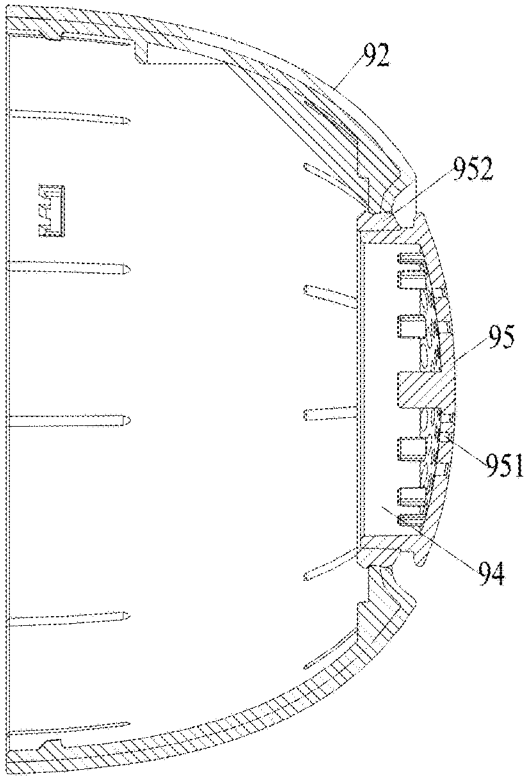
FIG. 55 is a sectional view of the filtering-cotton cover in FIG. 54 installed to the gas-inlet decorating member in FIG. 15.

The filtering-cotton cover 95 is preferably detachably installed to the gas-inlet decorating member 92. Particularly, for example, as shown in FIGS. 54 and 55, a plurality of protrusions 952 may be disposed on the periphery of the filtering-cotton cover 95, and the filtering-cotton cover 95 may implement interference fit with the gas inlet of the gas-inlet decorating member 92 via the protrusions 952.

Referring to FIGS. 15, 38 and 45-49, in order to further enhance the fastness and the reliability of the assembling between the upper housing 81, the middle housing 82 and the lower housing 83, the upper housing 81, the middle housing 82 and the lower housing 83 may be further connected by the bolt 88, the upper housing 81 may be provided with an upper-housing fixing hole 8116 for inserting the bolt 88, the middle housing 82 may be provided with a middle-housing fixing hole 824 for inserting the bolt 88, and the lower housing 83 may be provided with a lower-housing fixing hole 837 for inserting the bolt 88.

Figure 56:
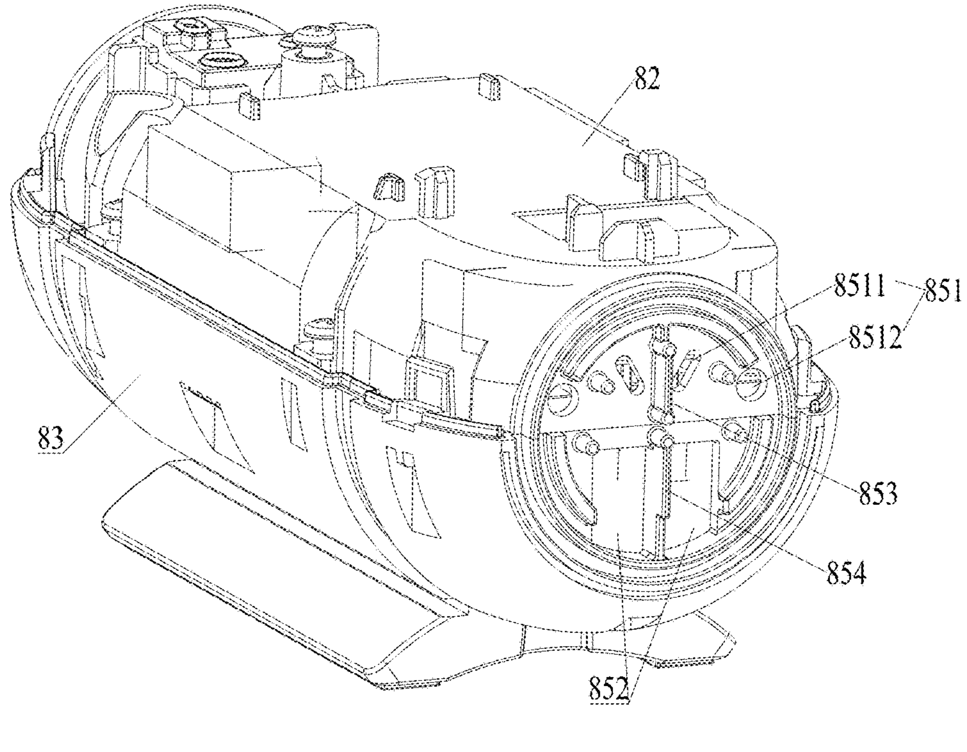
FIG. 56 is a perspective view of the assembling of the middle housing and the lower housing according to another embodiment of the present disclosure.

FIG. 56 shows a perspective view of the assembling of the middle housing 82 and the lower housing 83 according to another embodiment of the present disclosure, wherein except the structure at the gas-inlet end walls of the middle housing 82 and the lower housing 83, the other structures are substantially the same as the structures shown in FIG. 51. The gas-inlet end walls refer to the side walls of the middle housing 82 and the lower housing 83 that are located at the gas-inlet end (i.e., the right-side walls shown in FIGS. 51 and 56).

Figure 57:
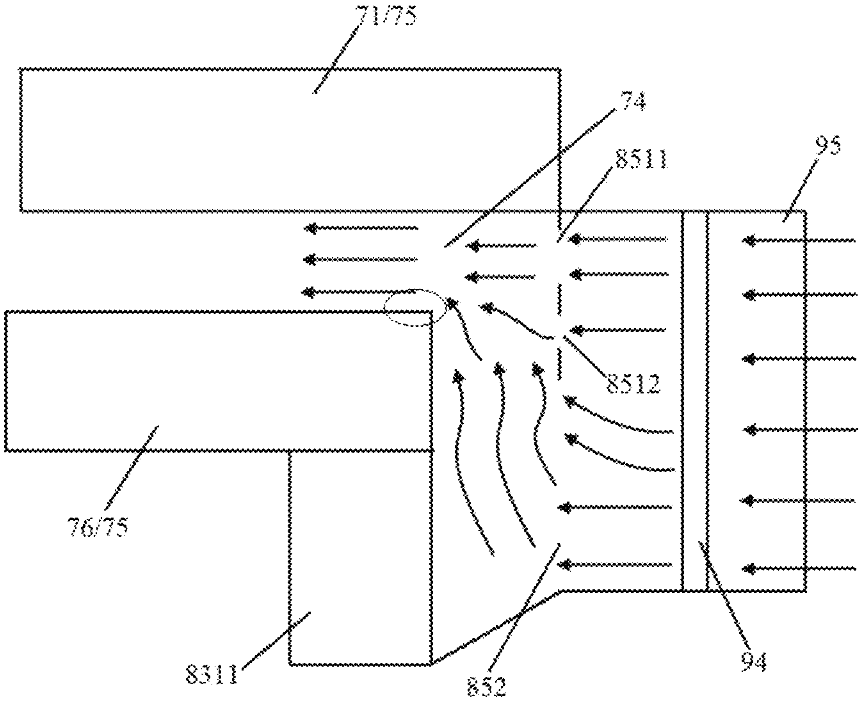
FIG. 57 is a schematic diagram of the local gas flow direction of a ventilating device comprising the middle housing and the lower housing in FIG. 56.
Figure 58:
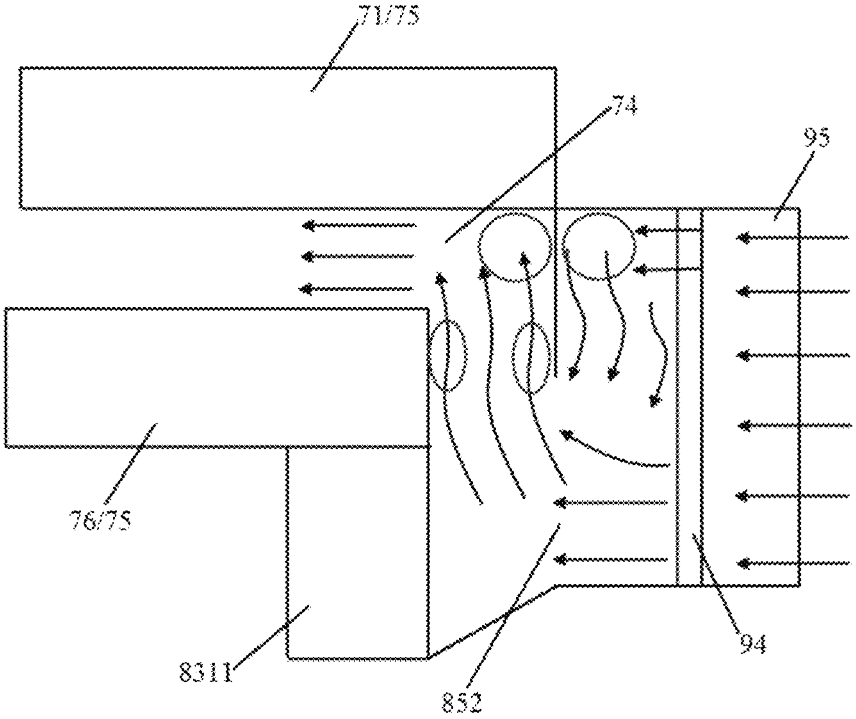
FIG. 58 is a schematic diagram of the local gas flow direction of a ventilating device comprising the middle housing and the lower housing in FIG. 51.

When the decorating assembly 90 is disposed outside the housing assembly 80, referring to FIG. 57 or 58, a chamber is formed between the gas-inlet end wall of the middle housing 82 and the gas-inlet end wall of the lower housing 83 and the filtering member of the decorating assembly 90. In the embodiment shown in FIG. 51, the gas inlet 85 of the housing assembly 80 is merely disposed in the gas-inlet end wall of the lower housing 83. After the gas entering via the through hole 951 in the filtering-cotton cover 95 has passed through the filtering cotton 94, part of the gas flow directly impacts the gas-inlet end wall of the middle housing 82, and the chamber between the gas-inlet end wall and the filtering member is small, whereby eddy current is easily generated at the corners. Subsequently, the gas flow enters the housing assembly via the gas inlet in the lower housing 83, and reaches the interior of the air passage 74. Due to the plurality of corners, most of the gas flow is in the state of disorder, and eddy current is serious, especially at the circular area in FIG. 58, which generates a large amount of noise.

However, in the embodiment shown in FIG. 56, the gas-inlet end wall of the middle housing 82 is disposed with a middle-housing gas inlet 851, the gas-inlet end wall of the lower housing 83 is provided with a lower-housing gas inlet 852, and the middle-housing gas inlet 851 and the lower-housing gas inlet 852 together form the gas inlet 85 of the housing assembly 80. By disposing the gas inlet at both of the middle housing 82 and the lower housing 83, not only the gas-intake area of the housing assembly 80 may be increased, but also the eddy current at the corners of the gas-inlet end wall may be reduced, thereby reducing the generation of the derivative noise.

In order to further divide the gas flow, to reduce eddy current, a dividing plate assembly may be provided inside the chamber between the gas-inlet end wall of the middle housing 82 and the gas-inlet end wall of the lower housing 83 and the filtering member, the dividing plate assembly partitions the chamber into at least two areas, the gas-inlet end wall of the middle housing 82 that is located in each of the areas is provided with at least one middle-housing gas inlet 851, and the gas-inlet end wall of the lower housing 83 that is located in each of the areas is provided with at least one lower-housing gas inlet 852.

Particularly, as shown in FIG. 56, the dividing plate assembly partitions the chamber between the gas-inlet end wall and the filtering member equally into a left area and a right area in the horizontal direction, the dividing plate assembly includes a first splitter plate 853 and a second splitter plate 854, the first splitter plate 853 is formed protrusively on the outer side surface of the gas-inlet end wall of the middle housing 82 and extends in the vertical direction, and the second splitter plate 854 is formed protrusively on the outer side surface of the gas-inlet end wall of the lower housing 83 and extends in the same direction as the extension direction of the first splitter plate 853. Accordingly, the gas flow entering the chamber may be divided by the first splitter plate 853 and the second splitter plate 854 into the left area and the right area, which may prevent or reduce gas-flow disturbance, and reduce the eddy-current generating area, thereby reducing the generation of the derivative noise, to achieve the purpose of noise reduction.

Preferably, the middle-housing gas inlets 851 located in the left area and the right area are disposed symmetrically with each other, and the lower-housing gas inlets 852 located in the left area and the right area are disposed symmetrically with each other.

As shown in FIG. 56, in each of the areas two middle-housing gas inlets 851 may be provided, one of the middle-housing gas inlets 851 may be an inclined elongate through hole 8511, the other of the middle-housing gas inlets 851 may be a circular through hole 8512, the two inclined elongate through holes 8511 in the left area and the right area are disposed symmetrically with each other, and the two circular through holes 8512 in the left area and the right area are disposed symmetrically with each other. By disposing the two middle-housing gas inlets 851 to form in the different shapes, the gas flow may generate derivative noises of different frequency bands to offset the noise generated by the fan 40. In addition, in each of the areas a lower-housing gas inlet 852 may be provided. The lower-housing gas inlet 852 may be configured to be provided with a larger size, to play a role as the main gas inlet of the housing assembly, and the middle-housing gas inlets 851 may be configured to have a smaller size, to serve as auxiliary gas inlets.

As shown in FIG. 57, after the gas entering via the through hole 951 in the filtering-cotton cover 95 passed through the filtering cotton 94, when it is continuing to advance, part of the gas enters the housing assembly via the middle-housing gas inlets 851, part of the gas enters the housing assembly via the lower-housing gas inlet 852, and subsequently the multiple gas flows converge at the gas-inlet end of the air passage 74. The middle-housing gas inlets 851, in an aspect, increase the ventilation area to reduce the gas resistance, and in another aspect, reduce the eddy-current area at the right-angle corners, to implement further denoising. Furthermore, due to the inclined elongate through holes 8511 and the circular through holes 8512, when the gas flow is flowing into the gas inlet of the air passage 74, a three-way confluence is formed, and the serious-eddy-current area is pushed forwardly to the circle in FIG. 57. Due to the function of flow dividing of the plurality of first partition plates 743 and second partition plates 745 of the noise reducing structure 70, the serious-eddy-current area is weakened or eliminated, thereby implementing further denoising.

In the above embodiment, by symmetrically disposing the middle-housing gas inlets 851 and the lower-housing gas inlet 852, the originally chaotic mixed-gas-flow area may be artificially adjusted into a turbulence transition state in which the frequency bands are similar and the wave forms are opposite at the gas-inlet end of the air passage 74, thereby implementing the superposing weakening of the noise.

Furthermore, by forming the three-way confluence when the gas flow is flowing into the gas inlet of the air passage 74, and through the different hole sizes of the middle-housing gas inlets 851 and the lower-housing gas inlet 852, the sudden change of the cross section of the gas-flow channel may be implemented, to form a resistance sound muting structure, to denoise the outwardly transmitting noise of the fan, to achieve further denoising of the breathing machine.

The preferable embodiments of the present disclosure have been described in detail above with reference to the drawings. However, the present disclosure is not limited to the particular details of the above embodiments. In the scope of the technical concept of the present disclosure, the technical solutions of the present disclosure may have various simple variations, and all of those simple variations fall in the protection scope of the present disclosure.

In addition, it should be noted that the particular technical features described in the particular embodiments, subject to no contradiction, may be combined in any feasible way. In order to avoid unnecessary repeating, the feasible modes of combination will not be described further herein.

Furthermore, the different embodiments of the present disclosure may also be combined in any way, and, as long as the combinations do not depart from the concept of the present disclosure, they should also be considered as the contents disclosed by the present disclosure.

What is claimed is:

1. A ventilation-treatment device, wherein the ventilation-treatment device comprises a noise reducing structure, wherein the noise reducing structure comprises a first micropore plate, the first micropore plate is provided with a first plate surface and a second plate surface which are opposite to each other, the first plate surface is configured for forming a first chamber, the second plate surface is for forming an air passage, to allow gas inside the air passage to flow along the second plate surface, and the first micropore plate is provided with a plurality of first micro-through holes communicate with the first chamber and the air passage;

wherein the ventilation-treatment device further comprises a ventilating tube assembly and a fan, a gas-inlet port of the ventilating tube assembly communicates with a gas outlet of the fan, and the air passage communicates with a gas inlet of the fan; and the ventilation-treatment device further comprises a housing assembly, the housing assembly comprises a cavity, and a gas inlet and a gas outlet that communicate with the cavity, the noise reducing structure, the ventilating tube assembly and the fan are disposed inside the cavity, the air passage communicates with the gas inlet of the housing assembly and the gas inlet of the fan, and a gas-outlet port of the ventilating tube assembly communicates with the gas outlet of the housing assembly; and the housing assembly further comprises a middle housing and a lower housing which are configured to form the cavity, the middle housing detachably covers a top of the lower housing, a gas-inlet end wall of the middle housing is provided with a middle-housing gas inlet configured to communicate with the cavity, a gas-inlet end wall of the lower housing is provided with a lower-housing gas inlet configured to communicate with the cavity, and the middle-housing gas inlet and the lower-housing gas inlet form the gas inlet of the housing assembly together; and the ventilation-treatment device further comprises a decorating assembly, the decorating assembly is configured to encircle the housing assembly, and is provided with a gas inlet and a gas outlet that correspond to the gas inlet and the gas outlet of the housing assembly, the decorating assembly comprises a filtering member, and the filtering member is disposed at the gas inlet of the decorating assembly;

wherein a chamber is formed between the gas-inlet end wall of the middle housing and the gas-inlet end wall of the lower housing and the filtering member, a dividing plate assembly is disposed inside the chamber, the dividing plate assembly is configured to partition the chamber into at least two areas, the gas-inlet end wall of the middle housing that is located in each of the at least two areas is disposed with the middle-housing gas inlet, and the gas-inlet end wall of the lower housing that is located in the at least two areas of the chamber is disposed with the lower-housing gas inlet; wherein, the middle-housing gas inlet and the lower-housing gas inlet are provided in either singular or plural.

2. The ventilation-treatment device according to claim 1, wherein the dividing plate assembly is configured to partition the chamber equally into a left area and a right area in a horizontal direction, the dividing plate assembly comprises a first splitter plate and a second splitter plate, the first splitter plate is formed protrusively on an outer side surface of the gas-inlet end wall of the middle housing and extends in a vertical direction, the second splitter plate is formed protrusively on an outer side surface of the gas-inlet end wall of the lower housing and extends in a same direction as an extension direction of the first splitter plate, the middle-housing gas inlets located in the left area and the right area are disposed symmetrically with each other, and the lower-housing gas inlets located in the left area and the right area are disposed symmetrically with each other.

3. The ventilation-treatment device according to claim 1, wherein the noise reducing structure comprises a first back plate, and the first back plate is positioned on a side of the first plate surface of the first micropore plate, to form the first chamber together with the first plate surface.

4. The ventilation-treatment device according to claim 3, wherein the first chamber is filled with a sound absorbing cotton.

5. The ventilation-treatment device according to claim 3, wherein the noise reducing structure comprises a second micropore plate, the second micropore plate is positioned between the first micropore plate and the first back plate, and is configured to partition the first chamber into an upper chamber close to the first micropore plate and a lower chamber close to the first back plate, and the second micropore plate is provided with a plurality of second micro-through holes communicating with the upper chamber and the lower chamber.

6. The ventilation-treatment device according to claim 5, wherein the upper chamber and the lower chamber are filled with a sound absorbing cotton.

7. The ventilation-treatment device according to claim 1, wherein the noise reducing structure comprises a second micropore plate, the second micropore plate is positioned on a side of the second plate surface of the first micropore plate, to form the air passage together with the second plate surface, and the second micropore plate is provided with a plurality of second micro-through holes communicating with the air passage.

8. The ventilation-treatment device according to claim 7, wherein, the noise reducing structure comprises a second back plate, the second back plate is positioned on one side of the second micropore plate that is away from the first micropore plate, to form a second chamber between the second micropore plate and the second back plate, and the second chamber communicates with the air passage via the plurality of second micro-through holes; and/or the first micropore plate and the second micropore plate are installed to cooperatively seal the air passage circumferentially, and a gas inlet and a gas outlet which communicate with the air passage are formed at two opposite ends.

9. The ventilation-treatment device according to claim 8, wherein, the second chamber is filled with a sound absorbing cotton, and/or the noise reducing structure comprises a plurality of first partition plates, the plurality of first partition plates are disposed inside the air passage and extend in a flow direction of a gas inside the air passage, respectively, and the plurality of first partition plates are disposed at intervals to partition the air passage into a plurality of branch air passages.

10. The ventilation-treatment device according to claim 9, wherein the noise reducing structure comprises a plurality of second partition plates, the plurality of second partition plates are disposed inside the plurality of branch air passages, respectively, the plurality of second partition plates are disposed at intervals and parallel to the plurality of first partition plates, both the plurality of first partition plates and the plurality of second partition plates are disposed to extend from the gas inlet to the gas outlet, and an extension length of the plurality of second partition plates is less than an extension length of the plurality of first partition plates.

* * * * *